(12) United States Patent
Neumann

(10) Patent No.: US 11,929,170 B2
(45) Date of Patent: Mar. 12, 2024

(54) METHODS AND SYSTEMS FOR SELECTING AN AMELIORATIVE OUTPUT USING ARTIFICIAL INTELLIGENCE

(71) Applicant: Kenneth Neumann, Lakewood, CO (US)

(72) Inventor: Kenneth Neumann, Lakewood, CO (US)

(73) Assignee: KPN Innovations, LLC, Longwood (CO)

( * ) Notice: Subject to any disclaimer, the term of this patent is extended or adjusted under 35 U.S.C. 154(b) by 1208 days.

(21) Appl. No.: 16/548,289

(22) Filed: Aug. 22, 2019

(65) Prior Publication Data
US 2021/0057048 A1    Feb. 25, 2021

(51) Int. Cl.
| | | |
|---|---|---|
| *G06N 20/00* | (2019.01) | |
| *G06F 18/2113* | (2023.01) | |
| *G06F 18/214* | (2023.01) | |
| *G06N 3/08* | (2023.01) | |
| *G06V 10/764* | (2022.01) | |
| *G06V 10/774* | (2022.01) | |
| *G06V 10/778* | (2022.01) | |

(Continued)

(52) U.S. Cl.
CPC ......... *G16H 50/20* (2018.01); *G06F 18/2113* (2023.01); *G06F 18/214* (2023.01); *G06N 3/08* (2013.01); *G06N 20/00* (2019.01); *G06V 10/764* (2022.01); *G06V 10/774* (2022.01); *G06V 10/7784* (2022.01); *G06V 10/7788* (2022.01); *G16B 40/00* (2019.02); *G16H 20/00* (2018.01); *G16H 50/00* (2018.01); *G16H 50/30* (2018.01)

(58) Field of Classification Search
USPC ......................................................... 706/15
See application file for complete search history.

(56) References Cited

U.S. PATENT DOCUMENTS

| | | |
|---|---|---|
| 7,844,560 B2 | 11/2010 | Krishnan et al. |
| 8,744,867 B2 | 6/2014 | Spertus |

(Continued)

OTHER PUBLICATIONS

Mobadersany, et al. Predicting cancer outcomes from histology and genomics using convolutional networks; https://www.pnas.org/content/pnas/115/13/E2970.full.pdf; Mar. 27, 2018.

(Continued)

*Primary Examiner* — David R Vincent
(74) *Attorney, Agent, or Firm* — Caldwell Intellectual Property Law

(57) ABSTRACT

A system for selecting an ameliorative output using artificial intelligence includes at least a server configured to receive at least a prognostic output. At least a server is configured to generate a plurality of ameliorative outputs as a function of at least a prognostic output wherein the plurality of ameliorative outputs include at least a short-term indicator and at least a long-term indicator. At least a server is configured to receive at least a user life element datum wherein the at least a user life element datum includes at least a user life quality response. At least a server is configured to generate a loss function of the plurality of short-term indicators and the plurality of long-term indicators using at least a user life element datum. At least a server is configured to select at least an ameliorative output from a plurality of ameliorative outputs to minimize the loss function.

20 Claims, 16 Drawing Sheets

(51) Int. Cl.
*G16B 40/00* (2019.01)
*G16H 20/00* (2018.01)
*G16H 50/00* (2018.01)
*G16H 50/20* (2018.01)
*G16H 50/30* (2018.01)

(56) References Cited

U.S. PATENT DOCUMENTS

| | | |
|---|---|---|
| 8,986,186 B2 | 3/2015 | Zhang et al. |
| 9,468,776 B2 | 10/2016 | Fredriksson |
| 10,046,177 B2 | 8/2018 | Sjölund et al. |
| 2006/0026036 A1 | 2/2006 | Mahmood |
| 2008/0319796 A1* | 12/2008 | Stivoric ............... A61B 5/7475 705/2 |
| 2012/0010528 A1 | 1/2012 | Donovan et al. |
| 2014/0156304 A1* | 6/2014 | Michon ................. G06Q 10/10 705/3 |
| 2014/0275700 A1 | 9/2014 | Nord et al. |
| 2015/0161331 A1 | 6/2015 | Oleynik |
| 2017/0083682 A1 | 3/2017 | McNutt et al. |
| 2017/0329905 A1 | 11/2017 | Passerini et al. |
| 2018/0068083 A1* | 3/2018 | Cohen .................... G16B 50/00 |
| 2018/0296320 A1 | 10/2018 | Gupta et al. |

OTHER PUBLICATIONS

Smith et al., A decision aid for intensity-modulated radiation-therapy plan selection in prostate cancer based on a prognostic Bayesian network and a Markov model; https://www.ncbi.nlm.nih.gov/pmc/articles/PMC2684564/; Jun. 1, 2019.

Rockne et al.; Predicting efficacy of radiotherapy in individual glioblastoma patients in vivo: a mathematical modeling approach; https://www.ncbi.nlm.nih.gov/pmc/articles/PMC3786554/; May 18, 2010.

* cited by examiner

METHODS AND SYSTEMS FOR SELECTING AN AMELIORATIVE OUTPUT USING ARTIFICIAL INTELLIGENCE

FIELD OF THE INVENTION

The present invention generally relates to the field of artificial intelligence. In particular, the present invention is directed to methods and systems for selecting an ameliorative output using artificial intelligence.

BACKGROUND

Accurate selection of ameliorative outputs can be challenging. Selection can also be hampered by user preferences for particular outputs. Inaccurate selection can ultimately frustrate users and lead to unsuccessful consequences.

SUMMARY OF THE DISCLOSURE

In an aspect, A system for selecting an ameliorative output using artificial intelligence the system comprising at least a server, the at least a server designed and configured to receive at least a prognostic output. At least a server is designed and configured to generate a plurality of ameliorative outputs associated with a plurality of short-term indicators and a plurality of long-term indicators as a function of the at least a prognostic output wherein each ameliorative output of the plurality of ameliorative outputs includes at least a short-term indicator of the plurality of short-term indicators and at least a long-term indicator of the plurality of long-term indicators. At least a server is designed and configured to receive at least a user life element datum wherein the at least a user life element datum further comprises at least a user life quality response. At least a server is designed and configured to generate a loss function as a function of the plurality of short-term indicator and the plurality of long-term indicators using the at least a user life element datum. At least a server is designed and configured to select at least an ameliorative output from the plurality of ameliorative outputs to minimize the loss function.

In an aspect, a method of selecting an ameliorative output using artificial intelligence the method including receiving by at least a server at least a prognostic output. The method including generating by the at least a server a plurality of ameliorative outputs, the plurality of ameliorative outputs associated with a plurality of short-term indicators and a plurality of long-term indicators, as a function of the at least a prognostic output wherein each ameliorative output of the plurality of ameliorative outputs includes at least a short-term indicator of the plurality of short-term indicators and at least a long-term indicator of the plurality of long-term indicators. The method including receiving by the at least a server at least a user life element datum wherein the at least a user life element datum further comprises at least a user life quality response. The method including generating by the at least a server a loss function of the plurality of short-term indicators and the plurality of long-term indicators using the at least a user life element datum. The method including minimizing by the at least a server the loss function. The method including selecting by the at least a server at least an ameliorative output from the plurality of ameliorative outputs to minimize the loss function.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for selecting an ameliorative output using artificial intelligence. In an embodiment at least a server receives at least a prognostic output wherein the at least a prognostic output includes at least a short-term output and at least a long-term output. At least a server generates a plurality of ameliorative outputs as a function of at least a prognostic output. Plurality of ameliorative outputs include at least a short-term indicator and at least a long-term indicator. At least a server receives at least a user life element datum wherein the at least a user life element datum includes at least a user life quality response. At least a server generates a loss function as a function of at least a prognostic output and at least a user life quality datum and minimizes the loss function. At least a server selects at least an ameliorative output from a plurality of ameliorative outputs as a function of minimizing a loss function.

Figure 1:
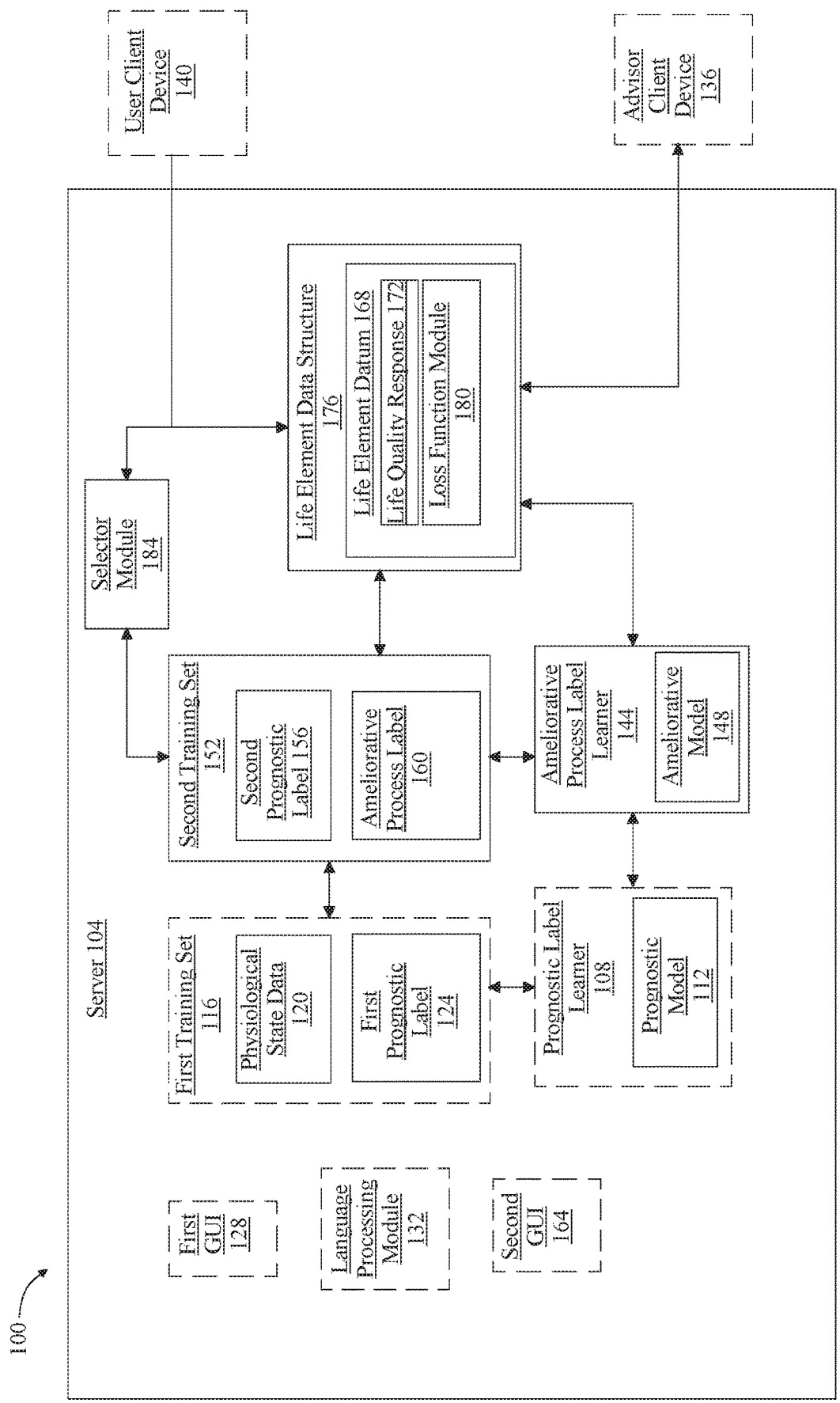
FIG. 1 is a block diagram illustrating an exemplary embodiment of a system for selecting an ameliorative output using artificial intelligence.

Referring now to the drawings, FIG. 1 illustrates an exemplary embodiment of a system 100 for selecting an ameliorative output using artificial intelligence. System 100 includes at least a server 104. At least a server 104 may include any computing device as described herein, including without limitation a microcontroller, microprocessor, digital signal processor (DSP) and/or system on a chip (SoC) as described below. At least a server 104 may be housed with, may be incorporated in, or may incorporate one or more sensor of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 may include one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server 104 and/or one or more modules operating thereon may be designed and/or configured to perform any method, method step, or sequence of method steps in any embodiment described in this disclosure, in any order and with any degree of repetition. For instance, at least a server 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 and/or one or more modules operating thereon may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, at least a server is configured to receive at least a prognostic output. In an embodiment, at least a prognostic output further comprises at least a short-term output and at least a long-term output. A prognostic output, as used herein, includes an element of data identifying and/or describing a current, incipient, or probable future medical condition affecting a person; medical condition may include a particular disease, one or more symptoms associated with a syndrome, a syndrome, and/or any other measure of current or future health and/or healthy aging. At least a prognostic output may be associated with a physical and/or somatic condition, a mental condition such as a mental illness, neurosis, or the like, or any other condition affecting human health that may be associated with one or more elements of physiological state data 120 as described in further detail below. Conditions associated with prognostic outputs may include, without limitation one or more diseases, defined for purposes herein as conditions that negatively affect structure and/or function of part or all of an organism. Conditions associated with prognostic outputs may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic outputs may be associated with one or more immune disorders, including without limitation immunodeficiencies and/or auto-immune conditions. Prognostic outputs may be associated with one or more metabolic disorders. Prognostic outputs may be associated with one or more endocrinal disorders. Prognostic outputs may be associated with one or more cardiovascular disorders. Prognostic outputs may be associated with one or more respiratory disorders. Prognostic outputs may be associated with one or more disorders affecting connective tissue. Prognostic outputs may be associated with one or more digestive disorders. Prognostic outputs may be associated with one or more neurological disorders such as neuromuscular disorders, dementia, or the like. Prognostic outputs may be associated with one or more disorders of the excretory system, including without limitation nephrological disorders. Prognostic outputs may be associated with one or more liver disorders. Prognostic outputs may be associated with one or more disorders of the bones such as osteoporosis. Prognostic outputs may be associated with one or more disorders affecting joints, such as osteoarthritis, gout, and/or rheumatoid arthritis. Prognostic outputs may be associated with one or more cancers, including without limitation carcinomas, lymphomas, leukemias, germ cell tumor cancers, blastomas, and/or sarcomas. Prognostic outputs may include descriptors of latent, dormant, and/or apparent disorders, diseases, and/or conditions. Prognostic outputs may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic outputs as described in this disclosure.

Still referring to FIG. 1, at least a prognostic output may be stored in any suitable data and/or data type. For instance, and without limitation, at least a prognostic output may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic output may take; persons skilled in the art, upon reviewing the entirety of this disclosure, will be aware of various forms which may be suitable for use as at least a prognostic output consistently with this disclosure.

With continued reference to FIG. 1, at least a prognostic output includes at least a short-term output and at least a long-term output. A short-term output, as used herein, includes an element of data identifying and/or describing an aspect, consideration and/or complication of a prognostic output affecting a person in the immediate present and may be in need of immediate urgent care. A long-term output, as used herein, includes an element of data identifying and/or describing an aspect, consideration, and/or complication of a prognostic output affecting a person in the future and may need consideration at some future point in time. For instance and without limitation, a prognostic output such as Type 2 Diabetes Mellitus may include at least a short-term output that includes a need to lower elevated blood sugars immediately and a long-term output describing a need to monitor over the future cardiovascular complications frequently seen in individuals diagnosed with Diabetes Mellitus. In yet another non-limiting example, a prognostic output such as acute kidney failure may include at least a short-term output that includes a need to preserve kidney function and reverse kidney failure and a long-term output that includes a need to assess ability for a user to receive a kidney transplant. In yet another non-limiting example, a prognostic output such as Chron's disease may include at least a short-term output that includes a need to stop a flare up of the disease and associated symptoms and a long-term output that includes a need to reverse injury to the gastrointestinal tract and heal the colon.

With continued reference to FIG. 1, system 100 may include a prognostic label learner operating on at least a server 104 that may be utilized to generate a prognostic output. Generating prognostic output may include creating at least a prognostic machine learning model relating physiological state data to prognostic labels using at least a first training set. Generating a prognostic output may include receiving at least a biological extraction from a user and using at least a first training set and at least a prognostic machine-learning model and the at least a biological extraction to produce a prognostic output. Prognostic label learner 108 may include any hardware and/or software module. Prognostic label learner 108 is designed and configured to generate at least a prognostic output using machine-learning processes. A machine-learning process is a process that automatedly uses a body of data known as "training data" and/or a "training set" to generate an algorithm that will be performed by a computing device and/or module to produce outputs given data provided as inputs; this is in contrast to a non-machine-learning software program where the commands to be executed are determined in advance by a user and written in a programming language.

Still referring to FIG. 1, prognostic label learner 108 may be designed and configured to generate at least a prognostic output by creating at least a prognostic machine-learning model 112 relating physiological state data 120 to prognostic labels using a first training set and generating the at least a prognostic output using the prognostic machine-learning model 112; at least a prognostic machine-learning model 112 may include one or more models that determine a mathematical relationship between physiological state data 120 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, at least a server 104 and/or prognostic label learner 108 may select a prognostic machine-learning algorithm as a function of the at least a biological extraction. For example, a biological extraction such as a hair sample may be best suited for a particular machine-learning algorithm such as a hierarchical clustering model while a biological extraction such as a blood sample may be best suited for a particular machine-learning model such as a supervised machine-learning model. In an embodiment, biological extractions may be matched to machine-learning algorithms. In an embodiment, a first training set selected as a function of at least a biological extraction may be best suited for a particular machine-learning algorithm. For instance and without limitation, a biological extraction such as a tissue sample analysis that is utilized to select a first training set that contains a plurality of three data entries may be best suited for a supervised machine-learning algorithm while a biological extraction such as a blood sample analysis that is utilized to select a first training set that contains a plurality of three hundred data entries may be best suited for an unsupervised machine-learning clustering algorithm whereby clusters generated from the unsupervised machine-learning algorithm may then be utilized in a supervised machine-learning algorithm. In an embodiment, at least a server 104 and/or prognostic label learner 108 may select a machine-learning model that relates particular inputs to outputs. For example, at least a server 104 and/or prognostic label learner 108 may select a machine-learning model as a function of the sample contained within at least a biological extraction whereby a blood sample may be utilized to select a particular machine-learning model and a urine sample may be utilized to select a separate machine-learning model.

With continued reference to FIG. 1, machine-learning algorithms may generate prognostic output as a function of a classification of at least a prognostic label. Classification as used herein includes pairing or grouping prognostic labels as a function of a shared commonality. Classification may include for example, groupings, pairings, and/or trends between physiological data and current prognostic label, future prognostic label, and the like. In an embodiment, machine-learning algorithms may examine relationships between a future propensity of a user to develop a condition based on current user physiological data. Machine-learning algorithms may include any and all algorithms as performed by any modules, described herein for prognostic label learner 108. For example, machine-learning algorithms may relate fasting blood glucose readings of a user to user's future propensity to develop diabetes. Machine-learning algorithms may examine precursor condition and future propensity to develop a subsequent disorder. For example, machine-learning algorithms may examine a user diagnosed with chicken pox and user's future propensity to subsequently develop shingles. In yet another non-limiting example, machine-learning algorithms may examine infection with human papillomavirus (HPV) and subsequent cancer diagnosis. Machine-learning algorithms may examine a user's propensity to have recurring attacks of a disease or condition, for example a user with elevated uric acid levels and repeated attacks of gout. Machine-learning algorithms may examine user's genetic predisposition to develop a certain condition or disease. For example, machine-learning algorithms may examine presence of hereditary non-polyposis colorectal cancer (HNPCC) commonly known as lynch syndrome, and subsequent diagnosis of colorectal cancer. In yet another non-limiting example, machine-learning algorithms may examine presence of abnormal squamous cells and/or abnormal glandular cells in the cervix and subsequent development of cervical cancer. Machine-learning algorithms may examine progression of disease state, for example progression of human immunodeficiency virus (HIV) is marked by decline of CD4+T-Cells, with a count below 200 leading to a diagnosis of acquired immunodeficiency syndrome (AIDS). In yet another non-limiting example, progression of diabetes may be marked by increases of hemoglobin A1C levels with a level of 6.5% indicating a diagnosis of diabetes. Machine-learning algorithms may examine progression of disease by certain age groups. For example, progression of Multiple Sclerosis in users between the age of 20-30 as compared to progression of Multiple Sclerosis in users between the age of 70-80. Machine-learning algorithms may be examining progression of aging such as measurements of telomere length and/or oxidative stress levels and chance mortality risk. Machine-learning algorithms may examine development of co-morbid conditions when a disease or conditions is already present. For example, machine-learning algorithms may examine a user diagnosed with depression and subsequent diagnosis of a co-morbid condition such as migraines, generalized anxiety disorder, antisocial personality disorder, agoraphobia, obsessive-compulsive disorder, drug dependence alcohol dependence, and/or panic disorder. Machine-learning algorithms may examine a user's lifetime chance of developing a certain disease or condition, such as a user's lifetime risk of heart disease, Alzheimer's disease, diabetes and the like. Machine-learning algorithms may be grouped and implemented according to any of the methodologies as described below.

Continuing to refer to FIG. 1, machine-learning algorithm used to generate prognostic machine-learning model 112 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, prognostic label learner 108 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using a first training set; the trained network may then be used to apply detected relationships between elements of physiological state data 120 and prognostic labels. With continued reference to FIG. 1, prognostic label learner 108 may be configured to generate a plurality of prognostic outputs each containing a ranked prognostic probability score. Prognostic probability score may be generated as a function of at least a biological extraction, at least a first training set, and at least a prognostic machine-learning model. A prognostic probability score, as used herein, is a mathematical representation indicating a likelihood of a particular prognostic output associated with at least a biological extraction. Prognostic probability score may include predictive values indicating a likelihood of a given prognostic output. In an embodiment, prognostic label learner 108 may generate a plurality of prognostic outputs which may each be ranked such as for example based on a decreasing likelihood of having a particular prognostic output. For instance and without limitation, at least a biological extraction such as a blood sample showing an elevated fasting blood glucose level may be utilized by prognostic label learner 108 in combination with at least a first training set 116 and at least a prognostic machine-learning model to generate a plurality of prognostic outputs that include diabetes mellitus type 2, pancreatitis, and Cushing's syndrome, with each prognostic output including a prognostic probability score and ranked in deceasing order of likelihood. In an embodiment, prognostic probability score may be calculated based on prevalence and predictive values. Prevalence indicates the probability of having a particular prognosis, and may also be known as the prior probability of having a particular prognosis. Predictive value indicates the probability of a prognosis in an individual with a biological extraction outside of normal limits and which contains a biological extraction classifier label of "low," "elevated" and/or "abnormal." Negative predictive value indicates the probability of not having a prognosis, such as when at least a biological extraction contains a biological extraction classifier label of "normal." In an embodiment, prognostic probability score may be calculated using machine-learning methods which may include any of the machine-learning methods as described herein. For example, in an embodiment prognostic label learner 108 may generate a plurality of prognostic outputs each containing a ranked prognostic probability score generated as a function of at least a biological extraction, at least a first training set, and at least a prognostic machine-learning model. In an embodiment, generating prognostic output may include selecting a lazy-learning process as a function of at least a biological extraction, recording the lazy-learning process in the descriptor trail database, and generating the prognostic output using the lazy-learning process as a function of the at least a biological extraction.

With continued reference to FIG. 1, at least a server 104 and/or prognostic label learner 108 may be configured to select training data to generate prognostic output using a selected machine-learning process. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

With continued reference to FIG. 1, at least a server 104 and/or prognostic label learner 108 may be configured to select a first training set 116 including a plurality of first data entries, each first data entry of the first training set 116 including at least an element of physiological state data 120 and at least a correlated first prognostic label 124. At least an element of physiological state data 120 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data 120 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data 120 may include, without limitation, immune function data such as Interleukine-6 (IL-6), TNF-alpha, systemic inflammatory cytokines, and the like.

Continuing to refer to FIG. 1, physiological state data 120 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data 120 may include measures of glucose metabolism such as fasting glucose levels and/or hemoglobin A1-C (HbA1c) levels. Physiological state data 120 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data 120 may include measures of estimated glomerular filtration rate (eGFR). Physiological state data 120 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data 120 may include antinuclear antibody levels. Physiological state data 120 may include aluminum levels. Physiological state data 120 may include arsenic levels. Physiological state data 120 may include levels of fibrinogen, plasma cystatin C, and/or brain natriuretic peptide.

Continuing to refer to FIG. 1, physiological state data 120 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data 120 may include a measurement blood pressure, including without limitation systolic and diastolic blood pressure. Physiological state data 120 may include a measure of waist circumference. Physiological state data 120 may include body mass index (BMI). Physiological state data 120 may include one or more measures of bone mass and/or density such as dual-energy x-ray absorptiometry. Physiological state data 120 may include one or more measures of muscle mass. Physiological state data 120 may include one or more measures of physical capability such as without limitation measures of grip strength, evaluations of standing balance, evaluations of gait speed, pegboard tests, timed up and go tests, and/or chair rising tests.

Still viewing FIG. 1, physiological state data 120 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 120 may include one or more measures of psychological function or state, such as without limitation clinical interviews, assessments of intellectual functioning and/or intelligence quotient (IQ) tests, personality assessments, and/or behavioral assessments. Physiological state data 120 may include one or more psychological self-assessments, which may include any self-administered and/or automatedly computer-administered assessments, whether administered within system 100 and/or via a third-party service or platform.

Continuing to refer to FIG. 1, physiological state data 120 may include psychological data. Psychological data may include any data generated using psychological, neuropsychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chatrooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

With continued reference to FIG. 1, physiological state data 120 may include one or more evaluations of sensor, including measures of audition, vision, olfaction, gustation, vestibular function and pain. Physiological state data 120 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data 120 may include proteomic data, which as used herein, is data describing all proteins produced and/or modified by an organism, colony of organisms, or system of organisms, and/or a subset thereof. Physiological state data 120 may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data 120 of a person, and/or on prognostic labels and/or ameliorative processes as described in further detail below. Physiological state data 120 may include any physiological state data 120, as described above, describing any multicellular organism living in or on a person including any parasitic and/or symbiotic organisms living in or on the persons; non-limiting examples may include mites, nematodes, flatworms, or the like.

With continuing reference to FIG. 1, physiological state data 120 may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Examples of physiological state data 120 described in this disclosure are presented for illustrative purposes only and are not meant to be exhaustive. Persons skilled in the art, upon reviewing the entirety of this disclosure, will be aware of various additional examples of physiological state data 120 that may be used consistently with descriptions of systems and methods as provided in this disclosure.

Continuing to refer to FIG. 1, each element of first training set 116 includes at least a first prognostic label 124. A prognostic label, as described herein, is an element of data suitable for use as prognostic output as described above.

With continued reference to FIG. 1, in each first data element of first training set 116, at least a first prognostic label of the data element is correlated with at least an element of physiological state data 120 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the first training set 116. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 116 and/or first data element consistently with this disclosure.

In an embodiment, and still referring to FIG. 1, at least a server 104 may be designed and configured to associate at least an element of physiological state data 120 with at least a category from a list of significant categories of physiological state data 120. Significant categories of physiological state data 120 may include labels and/or descriptors describing types of physiological state data 120 that are identified as being of high relevance in identifying prognostic labels. As a non-limiting example, one or more categories may identify significant categories of physiological state data 120 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, at least a server 104 may receive the list of significant categories according to any suitable process; for instance, and without limitation, at least a server 104 may receive the list of significant categories from at least an expert. In an embodiment, at least a server 104 and/or a user device connected to at least a server 104 may provide a first graphical user interface 128, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. First graphical user interface 128 or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like With continued reference to FIG. 1, data information describing significant categories of physiological data, relationships of such categories to prognostic labels, and/or significant categories of prognostic labels may alternatively or additionally be extracted from one or more documents using a language processing module 132. Language processing module 132 may include any hardware and/or software module. Language processing module 132 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 132 may compare extracted words to categories of physiological data recorded at least a server 104, one or more prognostic labels recorded at least a server 104, and/or one or more categories of prognostic labels recorded at least a server 104; such data for comparison may be entered on at least a server 104 as described above using expert data inputs or the like. In an embodiment, one or more categories may be enumerated, to find total count of mentions in such documents. Alternatively or additionally, language processing module 132 may operate to produce a language processing model. Language processing model may include a program automatically generated by at least a server 104 and/or language processing module 132 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at least a server 104, or the like.

Still referring to FIG. 1, language processing module 132 and/or at least a server 104 may generate the language processing model by any suitable method, including without limitation a natural language processing classification algorithm; language processing model may include a natural language process classification model that enumerates and/ or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 132 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 132 may use a corpus of documents to generate associations between language elements in a language processing module 132, and at least a server 104 may then use such associations to analyze words extracted from one or more documents and determine that the one or more documents indicate significance of a category of physiological data, a given relationship of such categories to prognostic labels, and/or a given category of prognostic labels. In an embodiment, at least a server 104 may perform this analysis using a selected set of significant documents, such as documents identified by one or more experts as representing good science, good clinical analysis, or the like; experts may identify or enter such documents via graphical user interface as described above in reference to FIG. 9, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of physiological sample, which then may be subjected to ranking, comparison to thresholds and/or elimination as described above.

Still referring to FIG. 1, at least a server 104 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, at least a server 104 may be configured, for instance as part of receiving the first training set 116, to associate at least correlated first prognostic label 124 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result at least a server 104 may modify list of significant categories to reflect this difference.

With continued reference to FIG. 1, generating prognostic output may include receiving at least a biological extraction from a user. At least a biological extraction may include any element and/or elements of data suitable for use as at least an element of physiological state data 120 as described in more detail above. At least a biological extraction may include a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensor, magnetoencephalographic sensor, electrocardiographic sensor, electromyographic sensor, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, blood sugar, and/or blood pressure. At least a sensor may be configured to detect internal and/or external biomarkers and/or readings. At least a sensor may be a part of system 100 or may be a separate device in communication with system 100.

Still referring to FIG. 1, at least a biological extraction may include any data suitable for use as physiological state data 120 as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, at least a biological extraction may include assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensor tests. Persons skilled in the art, upon reviewing the entirety of this disclosure, will be aware of various additional examples of at least a physiological sample consistent with this disclosure.

With continued reference to FIG. 1, prognostic output may be received from another device, platform, and/or system in communication with system 100 utilizing any network topology as described throughout this disclosure. For instance and without limitation, prognostic output may be received from an advisor client device operated by an informed advisor. Advisor client device 136 may include, without limitation, a display in communication with at least a server, display may include any display as described here. Advisor client device 136 may include an additional computing device, such as a mobile device, laptop, desktop computer, or the like; as a non-limiting example, advisor client device 136 may be a computer and/or workstation operated by a medical professional. Output may be displayed on at least an advisor client device 136 using an output graphical user interface. Informed advisor is defined for the purposes of this disclosure as any person besides the user who has access to information useable to aid user in interaction with artificial intelligence advisory system. An informed advisor may include, without limitation, a medical professional such as a doctor, nurse, nurse practitioner, functional medicine practitioner, any professional with a career in medicine, nutrition, genetics, fitness, life sciences, insurance, and/or any other applicable industry that may contribute information and data to system 100 regarding medical needs. An informed advisor may include a spiritual or philosophical advisor, such as a religious leader, pastor, imam, rabbi, or the like. An informed advisor may include a physical fitness advisor, such as without limitation a personal trainer, instructor in yoga or martial arts, sports coach, or the like.

With continued reference to FIG. 1, system 100 may include at least a user client device 140. User client device 140 may include any device suitable for use as an advisor client device 136 as described above. User client device 140 may operate on system 100 and may receive an output such as prognostic output and/or ameliorative output. In an embodiment, user client device 140 may communicate with advisor client device 136 and/or system 100 over a network, including any of the networks as described herein. In an embodiment, prognostic output may be received from user client device 140.

With continued reference to FIG. 1, at least a server is designed and configured to generate a plurality of ameliorative outputs as a function of the at least a prognostic output wherein the plurality of ameliorative outputs includes at least a short-term indicator and at least a long-term indicator. With continued reference to FIG. 1, at least a server 104 is configured to generate an ameliorative output as a function of a prognostic output. Generating an ameliorative output includes selecting at least an ameliorative machine-learning process as a function of a prognostic label, recording the selected ameliorative machine-learning process in the descriptor trail database, and generating the ameliorative output using the selected ameliorative machine-learning process as a function of the prognostic output. Ameliorative outputs may be associated with various treatment options, medications, and/or lifestyle changes.

With continued reference to FIG. 1, generating an ameliorative output may be performed by an ameliorative label learner operating on at least a server 104. Ameliorative process label learner 144 may include any hardware or software module suitable for use as a prognostic label learner 108 as described above. Ameliorative process label learner 144 is a machine-learning module as described above; ameliorative process label learner 144 may perform any machine-learning process or combination of processes suitable for use by a prognostic label learner 108 as described above. For instance, and without limitation, and ameliorative process label learner 144 may be configured to create a ameliorative machine-learning model 148 relating prognostic labels to ameliorative labels using the second training set 152 and generate the at least an ameliorative output using the ameliorative machine-learning model 148; ameliorative machine-learning model 148 may be generated according to any process, process steps, or combination of processes and/or process steps suitable for creation of prognostic machine-learning model. In an embodiment, ameliorative process label learner 144 may use data from first training set 116 as well as data from second training set 152; for instance, ameliorative process label learner 144 may use lazy learning and/or model generation to determine relationships between elements of physiological data, in combination with or instead of prognostic labels, and ameliorative labels. Where ameliorative process label learner 144 determines relationships between elements of physiological data and ameliorative labels directly, this may determine relationships between prognostic labels and ameliorative labels as well owing to the existence of relationships determined by prognostic label learner 108. In an embodiment, generating an ameliorative output may include selecting a lazy-learning process as a function of at least a biological extraction, recording the lazy-learning process in a descriptor trail database, and generating the prognostic output using the lazy-learning process as a function of the at least a biological extraction.

With continued reference to FIG. 1, ameliorative process label learner 144 may be configured to generate a plurality of ameliorative outputs each including at least a short-term indicator and at least a long-term indicator. A short-term indicator, as used herein, includes an element of data describing the impact of a particular ameliorative output on a prognostic output in the short term, immediate, and acute present moment. A long-term indicator, as used herein, includes an element of data describing the impact of a particular ameliorative output on a prognostic output in the long term and future moment. Short-term indicator and/or long-term indicator may include a description of potential side effects, complications, contraindications and adverse events associated with a particular ameliorative output that may be present and/or absent at particular instances during treatment. For instance and without limitation, an ameliorative output such as a chemotherapeutic agent may include a short-term indicator that includes eradicating cancer cells and a long-term indicator that includes heart failure. In yet another non-limiting example, an ameliorative output such as an antibiotic utilized to treat an infection may contain a short-term indicator that includes stomach upset and diarrhea and a long-term indicator that includes possibility of developing chronic stomach upset and diarrhea because a *Clostridium Difficile* infection. In an embodiment, short-term indicator and/or long-term indicator may be associated with a numerical score, describing a probability of treatment success, ability to impact a particular prognostic output such as a particular reduction in blood sugar levels for a diabetic, and/or a particular probability of developing a side effect and/or co-morbid condition based on a particular ameliorative output. Prognostic improvement score may be generated as a function of at least a prognostic output, at least a second training set, and at least an ameliorative machine-learning model. Ameliorative process label learner 144 may generate a plurality of ameliorative outputs each containing a short-term indicator and a long-term indicator. In an embodiment, plurality of ameliorative outputs may be ranked in a particular order according to a numerical score given to an ameliorative output for a particular short-term indicator and a particular long-term indicator. For example, ameliorative process label learner may generate a plurality of ameliorative outputs and rank the plurality of ameliorative outputs in decreasing order of long-term indicators. In yet another non-limiting example, ameliorative process label learner may generate a plurality of ameliorative outputs and rank the plurality of ameliorative outputs in decreasing order of short-term indicators.

With continued reference to FIG. 1, selecting an ameliorative machine-learning process to generate ameliorative output may include selecting a second training set by at least a server 104 and/or ameliorative label learner. Second training set 152 including a plurality of second data entries. Each second data entry of the second training set 152 includes at least a second prognostic label; at least a second prognostic label 136 may include any label suitable for use as at least a first prognostic label 124 as described above. Each second data entry of the second training set 152 includes at least an ameliorative process label 160 correlated with the at least a second prognostic label, where correlation may include any correlation suitable for correlation of at least a first prognostic label 124 to at least an element of physiological data as described above. As used herein, an ameliorative process label 160 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

With continued reference to FIG. 1, ameliorative process label learner 144 and/or at least a server 104 may be configured to select an ameliorative machine-learning algorithm as a function of the prognostic label. Selecting an ameliorative machine-learning algorithm may include selecting a machine-learning algorithm to generate ameliorative model. For instance and without limitation, a first training set utilized to generate a prognostic output may be correlated to a second training set that may be utilized to generate ameliorative output which may be utilized to select an ameliorative machine-learning process. In yet another non-limiting example, a plurality of prognostic labels generated by prognostic label learner 108 may be utilized to select a particular machine-learning algorithm that will utilize the plurality of prognostic labels to generate a particular ameliorative output. In yet another non-limiting example, a prognostic output that contains very few ameliorative outputs such as a rare form of cancer may be utilized to select an unsupervised machine-learning algorithm which may be best suited such as a k-nearest neighbors algorithm to find potential ameliorative treatment options. In yet another non-limiting example, a prognostic output that may be associated with numerous treatment options such as diabetes may be best suited for a supervised machine-learning algorithm. Ameliorative process label learner 144 and/or at least a server 104 may select at least a machine-learning model as a function of inputs and outputs utilized by ameliorative process label to generate ameliorative model 148. For example, a particular prognostic output utilized as an input by ameliorative process learner 148 may be best suited for a particular machine-learning model. In yet another non-limiting example, a particular desired ameliorative output that will be generated by ameliorative process label learner 144 may be best suited for a different particular machine-learning model.

Continuing to refer to FIG. 1, in an embodiment at least a server 104 may be configured, for instance as part of selecting second training set 152, to associate the at least second prognostic label 156 with at least a category from a list of significant categories of prognostic labels. This may be performed as described above for use of lists of significant categories with regard to at least a first prognostic label. Significance may be determined, and/or association with at least a category, may be performed for prognostic labels in first training set 116 according to a first process as described above and for prognostic labels in second training set 152 according to a second process as described above.

Still referring to FIG. 1, at least a server 104 may be configured, for instance as part of selecting second training set 152, to associate at least a correlated ameliorative process label 160 with at least a category from a list of significant categories of ameliorative process labels 120. In an embodiment, at least a server 104 and/or a user device connected to at least a server 104 may provide a second graphical user interface 164 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 132 or the like as described above.

In an embodiment, and still referring to FIG. 1, at least a server 104 may extract at least a second data entry from one or more documents; extraction may be performed using any language processing method as described above. At least a server 104 may be configured, for instance as part of receiving second training set 152, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 120, and/or efficacy of ameliorative process labels 120 may be extracted from and/or determined from one or more medical history documents using any processes for language processing as described above; for instance, language processing module 132 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

With continued reference to FIG. 1, at least a server 104 may be configured, for instance as part of receiving second training set 152, to receive at least a second data entry of the plurality of second data entries from at least an expert. This may be performed, without limitation using second graphical user interface 164 as described above.

With continued reference to FIG. 1, at least a server 104 is configured to select training data including at least a first training set 116 and at least a second training set 152. At least a server 104 may be configured to select at least a first training set 116 as a function of at least a physically extracted sample contained within at least a biological extraction. For example, at least a biological extraction containing a stool sample may be utilized to select at least a first training set 116 that includes physiological state data 120 that includes a stool sample. In yet another non-limiting example, at least a biological extraction containing a urine sample may be utilized to select at least a first training set 116 that includes physiological state data 120 that includes a urine sample. Training data may be organized according to physiological categories and contained within a training set database as described in more detail below.

With continued reference to FIG. 1, at least a server 104 is configured to receive at least a user life element datum 168 wherein the at least a user life element datum 168 includes at least a user life quality response 172. A user life element datum, as used herein, includes any data describing a user's life criterion regarding health and wellness. Life criterion may include any principles, standards, and/or goals that a user aspires to achieve in regard to user's own health and wellness. For instance and without limitation, life criterion may include principles, standards, and/or goals surrounding life expectancy, education, standards of living, happiness levels, and the like. In an embodiment, life criterion may be received based on user input to questions and/or surveys based on user input generated at user client device 140. For example, a user may respond to particular life quality surveys such as The Physical Quality of Life Index (PQLI), The Happy Planet Index, Social Progress Index, The Popsicle Index and the like. A user life quality response, as used herein, includes any data describing a user's preference for health related quality of health life measures. Quality of health life measures may include views and preferences regarding life saving measures, lifesaving therapies, end of life measures, types of medical treatments to be received, end of life care, and the like. Life quality response 172 may include for example, a user response describing a user's desired quality of life, which may include for example a description of a user's preference for oral medications over intravenous medications or a response describing a user's input to not receive life-saving measures such as resuscitation during a surgery. Life quality response 172 may include indicators describing a user's preference to receive or not receive treatment for a terminal diagnosis. Life quality response 172 may include indicators describing a user's preference for a particular modality of treatment such as a preference for naturopathic treatments over conventional medicine.

With continued reference to FIG. 1, user life element datums may be stored in life element data structure 176. Life element data structure 176 may include any data structure capable of storing user life element datums including, for example and without limitation, linked lists, hash tables, vectors and the like. Life element data structure 176 may be implemented as a relational database, a key-value retrieval datastore such as a NOSQL database, or any other format or structure for use as a datastore that a person skilled in the art would recognize as suitable upon review of the entirety of this disclosure.

With continued reference to FIG. 1, system 100 may include a loss function module 180 operating on the at least a server 104. In an embodiment, loss function module 180 may be contained within life element data structure 176. At least a server 104 and/or loss function module 180 may be designed and configured to generate a loss function as a function of at least a prognostic output and at least a user life element datum 168 and minimize the loss function. Loss function module 180 may perform machine-learning algorithms using a loss function analysis utilizing linear regression to select at least an ameliorative output from a plurality of ameliorative outputs. In an embodiment, loss function module 180 may compare one or more user specific inputs to a mathematical expression representing an optimal combinations of user specific inputs and/or optimal ameliorative outputs. Mathematical expression may include a linear combination of variables, weighted by coefficients representing relative importance of each variable in selecting an optimal ameliorative output. For instance, a variable such as a life element datum 168 may be multiplied by a first coefficient representing the importance of a life element, a second user input such as a life quality response 172 may be multiplied by a second coefficient representing the importance of life quality, a degree of variance from an ameliorative output may be represented as another parameter, which may be multiplied by another coefficient representing the importance of that variable; persons skilled in the art, upon reviewing the entirety of this disclosure, will be aware of different variables that may be weighted by various coefficients. Use of a linear combination is provided only as an illustrative example; other mathematical expressions may alternative or additionally be used, including without limitation higher-order polynomial expressions or the like.

With continued reference to FIG. 1, mathematical expression may represent a loss function where a "loss function" is an expression of an output of which an optimization algorithm minimizes to generate an optimal result. As a non-limiting example, loss function module 180 may calculate variables of each of a plurality of user inputs and/or ameliorative outputs, calculate an output of mathematical expression using the variables, and select at least an ameliorative output that produces an output having the lowest size, according to a given definition of "size," of the sets of outputs representing each of the plurality of ameliorative outputs; size may, for instance, include absolute value, numerical size, or the like. Selection of different loss functions may result in identification of different ameliorative outputs as generating minimal outputs; for instance, where a user input such as a user life quality response 172 is associated in a first loss function with a large coefficient or weight, a user input such as a life quality response 172 having a small coefficient or weight may minimize the first loss function, whereas a second loss function user life element response has a smaller coefficient but degree of variance from life quality response 172 may produce a minimal output for a different ameliorative output having a larger coefficient for user life element response but more closely hewing to life quality response 172.

With continued reference to FIG. 1, each ameliorative output of the plurality of ameliorative outputs may be represented by a mathematical expression having the same form as mathematical expression; loss function module 180 may compare the former to the latter using an error function representing average difference between the two mathematical expressions. Error function may, as a non-limiting example, be calculated using the average difference between coefficients corresponding to each user input variables. An ameliorative output having a mathematical expression minimizing the error function may be selected, as representing an optimal expression of relative importance of variables to a system or user. In an embodiment, error function and loss function calculations may be combined; for instance, an ameliorative output resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to ameliorative output variables. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each variable to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of alimentary provision options.

With continued reference to FIG. 1, loss function module 180 may generate a loss function of user specific variables and minimize the loss function. Loss function module 180 select at least an ameliorative output using loss function analysis. Loss function analysis may measure changes in predicted values versus actual values, known as loss or error. Loss function analysis may utilize gradient descent to learn the gradient or direction that a cost analysis should take in order to reduce errors. Loss function analysis algorithms may iterate to gradually converge towards a minimum where further tweaks to the parameters produce little or zero changes in the loss or convergence by optimizing weights utilized by machine learning algorithms. Loss function analysis may examine the cost of the difference between estimated values, to calculate the difference between hypothetical and real values. Loss function module 180 may utilize variables to model relationships between prognostic outputs, life element datums, life quality response 172, and ameliorative outputs. In an embodiment loss function analysis may utilize variables that may impact user interactions and/or ameliorative outputs. Loss function analysis may be user specific so as to create algorithms and outputs that are customize to variables for an individual user. Variables may include any of the variables as described below in more detail below. Variables contained within loss function analysis may be weighted and given different numerical scores. Variables may be stored and utilized to predict subsequent outputs. Outputs may seek to select at least an optimal ameliorative output from a plurality of ameliorative outputs.

With continued reference to FIG. 1, at least a server 104 and/or life element data structure 176 may be configured to receive at least a user life element containing user responses that may be utilized to generate a loss function by loss function module 180, minimize the loss function, and select at least an ameliorative output as a function of minimizing the loss function. User life element datum 168 may include a user ameliorative effort indicator datum. An ameliorative effort indicator datum, as used herein, includes any user response describing a particular level of effort that a user is willing to devote to any given ameliorative output. Level of effort may include a certain quantity of time a user is willing to devote to an ameliorative output. For example, a user may respond that user will devote three hours per week to practicing a particular yoga sequence or a user may respond that user will devote one hour each week to preparing meals for the week. Level of effort may include a certain amount of resources a user is willing to devote to a particular ameliorative output. For example, a user may respond that user will put ten percent of user's salary towards a supplement regimen each month or a user may seek to spend five percent of user's paycheck one time towards equipment user may need to develop a meditation sequence. User life element datum 168 may include at least a user constitutional variance life datum. A user constitutional variance life datum, as used herein, includes a user's long-term longevity goal. Long-term longevity goal may include a particular health related achievement that a user hopes to achieve at some point in the future. For example, long-term longevity goal may include a user's desire to regulate user's insulin levels to avoid consistently high blood sugar readings within the next six months. In yet another non-limiting example, long-term longevity goal may include a user's desire to become more flexible by practicing yoga three days each week for the next twelve months. In an embodiment, at least a server and/or life element data structure 176 may be configured to receive at least a biological extraction from a user and generate a loss function as a function of the at least a biological extraction. At least a biological extraction may include any of the biological extractions as described above.

With continued reference to FIG. 1, system 100 may include selector module 184. Selector module 184 may include any hardware and/or software module. In an embodiment, selector module 184 and/or at least a server 104 may be designed and configured to select at least an ameliorative output from a plurality of ameliorative outputs as a function of minimizing a loss function. Selector module 184 may be configured to receive user inputs such as those generated at user client device that may also be utilized in selecting at least an ameliorative output. Selector module 184 may be configured to receive at least a datum of previous ameliorative history for a user and select at least an ameliorative output as a function of the at least a datum of previous ameliorative history. A datum of ameliorative history, as used herein, includes any data describing a previous ameliorative output that was utilized by a user. For example, a datum of ameliorative history may include a particular supplement that a user took for six months when a user experienced post-partum depression. In such an instance, datum of ameliorative history describing a particular supplement that a user took for six months for post-partum depression may be utilized to select at least an ameliorative output that contains the same supplement when user's symptoms return. In an embodiment, datum of ameliorative history may be stored within life element data structure 176. Selector module 184 may select at least at least an ameliorative output by matching at least a prognostic output to at least an ameliorative output containing at least a long-term indicator. For example, selecting module may match a prognostic output containing a particular long-term output to an ameliorative output containing at least a particular long-term indicator. For example, a prognostic output such as small intestinal bacterial overgrowth (SIBO) containing a long term indicator that includes a possible complication such as systemic *Candida* infection may be matched to an ameliorative output containing at least a particular long-term indicator that includes suppression of *Candida* as compared to an ameliorative output that contains a particular long-term indicator that is neutral in regards to suppression of *Candida*. In yet another non-limiting example, a prognostic output such as prostate cancer containing a long term indicator that includes a possible complication such as hair loss may be matched to an ameliorative output containing at least a long-term indicator that includes hair growth as compared to an ameliorative output that contains a long-term indicator such as hair loss. Selector module 184 mat select at least an ameliorative output as a function of ranking the plurality of ameliorative outputs and selecting at least an ameliorative output as a function of the ranking. In an embodiment, ranking may be done based on minimizing the loss function which may produce an output containing ameliorative outputs ranked. In yet another non-limiting example, ranking may be done based on specific calculations and/or characteristics associated with a particular ameliorative output.

With continued reference to FIG. 1, at least a server may be configured to receive at least a first ameliorative output containing at least a short-term indicator and at least a long-term indicator, generate a plurality of ameliorative output neutralizers as a function of the at least an ameliorative output wherein the plurality of ameliorative output neutralizers include at least a short-term indicator and at least a long-term indicator, a generate a loss function as a function of the at least a first ameliorative output and the plurality of ameliorative output neutralizers, minimize the loss function, and select at least an ameliorative output neutralizer from the plurality of ameliorative output neutralizers as a function of minimizing the loss function. An ameliorative output neutralizer, as used herein, includes any ameliorative output intended to minimize at least a long-term indicator containing a negative and/or unwanted consequence of at least a first ameliorative output. For instance and without limitation, a first ameliorative output selected by selector module, may contain at least a long-term indicator that includes a negative consequence such as symptoms of nausea. In such an instance, first ameliorative output selected by selector module may be utilized to generate a plurality of ameliorative output neutralizers that will help control long-term indicator of nausea. In yet another non-limiting example, a first ameliorative output such as a medication or treatment that is associated with serious adverse events such as chemotherapy that induces heart failure may be selected and utilized to generate a plurality of ameliorative output neutralizers that may help diminish and reduce the risk of developing heart failure over time. In such an instance, at least a server may generate a loss function as a function of at least a first ameliorative output and a plurality of ameliorative output neutralizers, minimize the loss function, and select at least an ameliorative output neutralizer. Generating at least an ameliorative output neutralizer may be done using any of the methodologies as described above for generating at least an ameliorative output. Loss function and minimizing the loss function may include any of the loss functions and steps for minimizing the loss function as described above.

Figure 2:
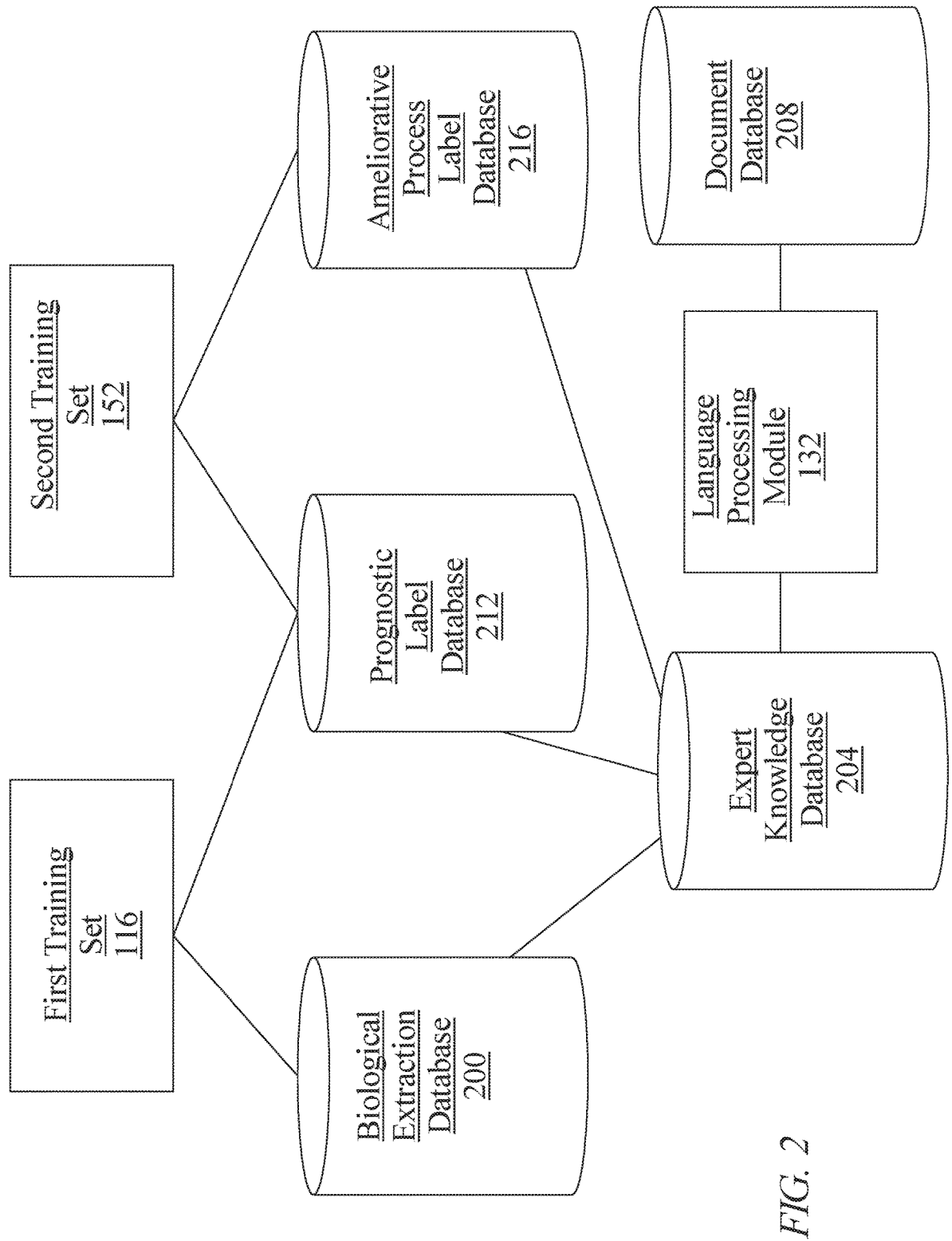
FIG. 2 is a block diagram illustrating embodiments of data storage facilities for use in disclosed systems and methods.

Referring now to FIG. 2, data incorporated in first training set 116 and/or second training set 152 may be incorporated in one or more databases. As a non-limiting example, one or elements of physiological state data 120 may be stored in and/or retrieved from a biological extraction database 200. A biological extraction database 200 may include any data structure for ordered storage and retrieval of data, which may be implemented as a hardware or software module. A biological extraction database 200 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 200 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a biological extraction database 200 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensor, and/or any other information concerning provenance and/or history of data acquisition. Persons skilled in the art, upon reviewing the entirety of this disclosure, will be aware of various ways in which data entries in a biological extraction database 200 may reflect categories, cohorts, and/or populations of data consistently with this disclosure.

With continued reference to FIG. 2, at least a server 104 and/or another device in system 100 may populate one or more fields in biological extraction database 200 using expert information, which may be extracted or retrieved from an expert knowledge database 204. An expert knowledge database 204 may include any data structure and/or data store suitable for use as a biological extraction database 200 as described below. Expert knowledge database 204 may include data entries reflecting one or more expert submissions of data such as may have been submitted according to any process described above in reference to FIG. 1, including without limitation by using first graphical user interface 128 and/or second graphical user interface 164. Expert knowledge database may include one or more fields generated by language processing module 132, such as without limitation fields extracted from one or more documents as described above. For instance, and without limitation, one or more categories of physiological data and/or related prognostic labels and/or categories of prognostic labels associated with an element of physiological state data 120 as described above may be stored in generalized from in an expert knowledge database 204 and linked to, entered in, or associated with entries in a biological extraction database 200. Documents may be stored and/or retrieved by at least a server 104 and/or language processing module 132 in and/or from a document database 208; document database 208 may include any data structure and/or data store suitable for use as biological extraction database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

With continued reference to FIG. 2, a prognostic label database 212, which may be implemented in any manner suitable for implementation of biological extraction database 200, may be used to store prognostic labels used in system 100, including any prognostic labels correlated with elements of physiological data in first training set 116 as described above; prognostic labels may be linked to or refer to entries in biological extraction database 200 to which prognostic labels correspond. Linking may be performed by reference to historical data concerning physiological samples, such as diagnoses, prognoses, and/or other medical conclusions derived from physiological samples in the past; alternatively or additionally, a relationship between a prognostic label and a data entry in biological extraction database 200 may be determined by reference to a record in an expert knowledge database 204 linking a given prognostic label to a given category of physiological sample as described above. Entries in prognostic label database 212 may be associated with one or more categories of prognostic labels as described above, for instance using data stored in and/or extracted from an expert knowledge database 204.

With continued reference to FIG. 2, first training set 116 may be populated by retrieval of one or more records from biological extraction database 200 and/or prognostic label database 212; in an embodiment, entries retrieved from biological extraction database 200 and/or prognostic label database 212 may be filtered and or select via query to match one or more additional elements of information as described above, so as to retrieve a first training set 116 including data belonging to a given cohort, demographic population, or other set, so as to generate outputs as described below that are tailored to a person or persons with regard to whom system 100 classifies physiological samples to prognostic labels as set forth in further detail below. Persons skilled in the art, upon reviewing the entirety of this disclosure, will be aware of various ways in which records may be retrieved from biological extraction database 200 and/or prognostic label database to generate a first training set 116 to reflect individualized group data pertaining to a person of interest in operation of system and/or method, including without limitation a person with regard to whom at least a physiological sample is being evaluated as described in further detail below. At least a server 104 may alternatively or additionally receive a first training set 116 and store one or more entries in biological extraction database 200 and/or prognostic label database 212 as extracted from elements of first training set.

With continued reference to FIG. 2, system 100 may include or communicate with an ameliorative process label database 216; an ameliorative process label database 216 may include any data structure and/or datastore suitable for use as a biological extraction database 200 as described above. An ameliorative process label database 216 may include one or more entries listing labels associated with one or more ameliorative processes as described above, including any ameliorative labels correlated with prognostic labels in second training set 152 as described above; ameliorative process labels may be linked to or refer to entries in prognostic label database 212 to which ameliorative process labels correspond. Linking may be performed by reference to historical data concerning prognostic labels, such as therapies, treatments, and/or lifestyle or dietary choices chosen to alleviate conditions associated with prognostic labels in the past; alternatively or additionally, a relationship between an ameliorative process label 160 and a data entry in prognostic label database 212 may be determined by reference to a record in an expert knowledge database 204 linking a given ameliorative process label 160 to a given category of prognostic label as described above. Entries in ameliorative process label database 216 may be associated with one or more categories of prognostic labels as described above, for instance using data stored in and/or extracted from an expert knowledge database 204.

With continued reference to FIG. 2, second training set 152 may be populated by retrieval of one or more records from prognostic label database 212 and/or ameliorative process label database 216; in an embodiment, entries retrieved from prognostic label database 212 and/or ameliorative process label database 216 may be filtered and or select via query to match one or more additional elements of information as described above, so as to retrieve a second training set 152 including data belonging to a given cohort, demographic population, or other set, so as to generate outputs as described below that are tailored to a person or persons with regard to whom system 100 classifies prognostic labels to ameliorative process labels as set forth in further detail below. Persons skilled in the art, upon reviewing the entirety of this disclosure, will be aware of various ways in which records may be retrieved from prognostic label database 212 and/or ameliorative process label database 216 to generate a second training set 152 to reflect individualized group data pertaining to a person of interest in operation of system and/or method, including without limitation a person with regard to whom at least a physiological sample is being evaluated as described in further detail below. At least a server 104 may alternatively or additionally receive a second training set 152 and store one or more entries in prognostic label database 212 and/or ameliorative process label database 216 as extracted from elements of second training set.

With continued reference to FIG. 2, at least a server 104 may receive an update to one or more elements of data represented in first training set 116 and/or second training set, and may perform one or more modifications to first training set 116 and/or second training set, or to biological extraction database 200, expert knowledge database 204, prognostic label database 212, and/or ameliorative process label database 216 as a result. For instance, a physiological sample may turn out to have been erroneously recorded; at least a server 104 may remove it from first training set, second training set, biological extraction database 200, expert knowledge database 204, prognostic label database 212, and/or ameliorative process label database 216 as a result. As a further example, a medical and/or academic paper, or a study on which it was based, may be revoked; at least a server 104 may remove it from first training set, second training set, biological extraction database 200, expert knowledge database 204, prognostic label database 212, and/or ameliorative process label database 216 as a result. Information provided by an expert may likewise be removed if the expert loses credentials or is revealed to have acted fraudulently.

Continuing to refer to FIG. 2, elements of data first training set, second training set, biological extraction database 200, expert knowledge database 204, prognostic label database 212, and/or ameliorative process label database 216 may have temporal attributes, such as timestamps; at least a server 104 may order such elements according to recency, select only elements more recently entered for first training set 116 and/or second training set, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Figure 3:
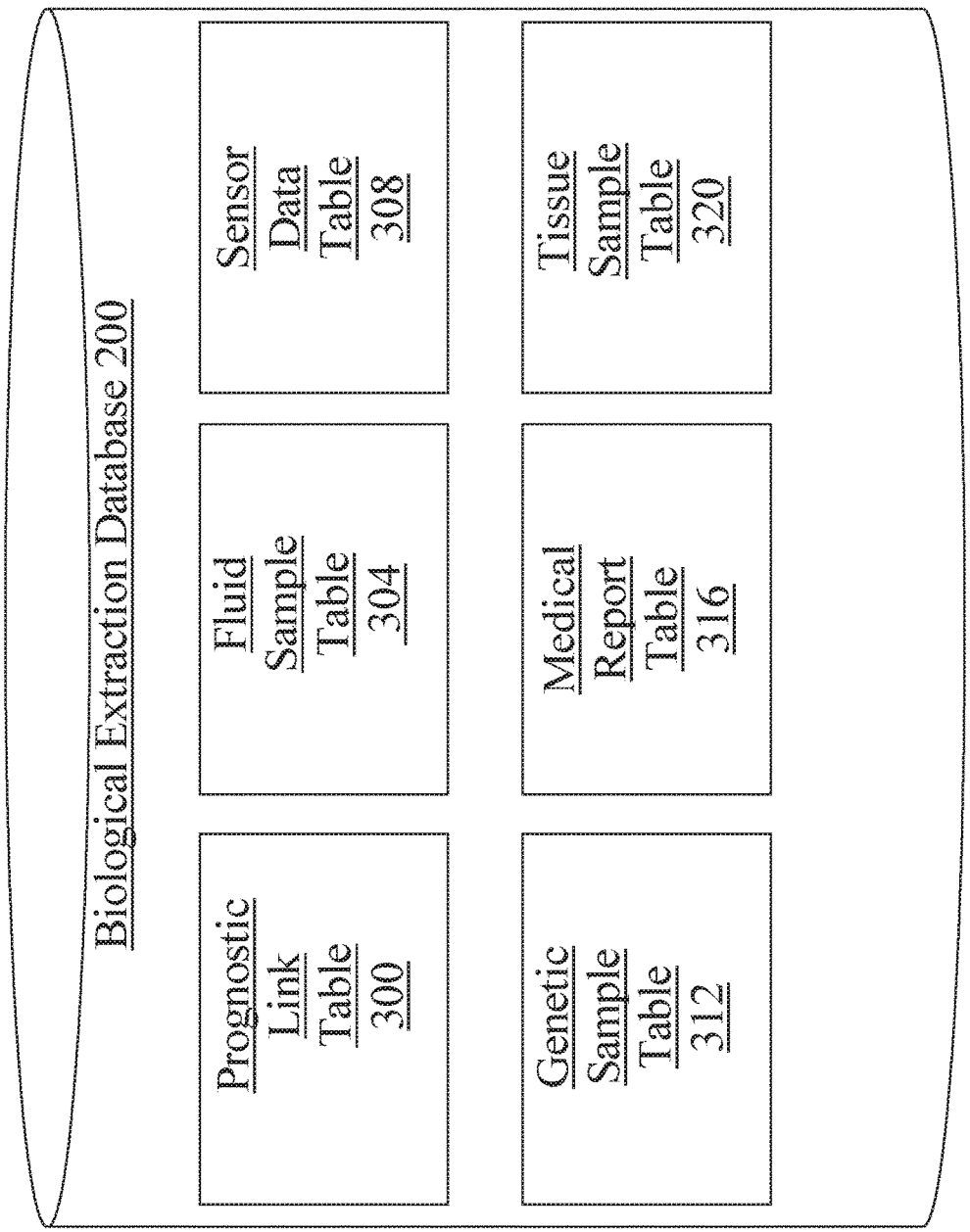
FIG. 3 is a block diagram illustrating an exemplary embodiment of a biological extraction database.

Referring now to FIG. 3, an exemplary embodiment of biological extraction database 200 is illustrated, which may be implemented, without limitation, as a hardware or software module. Biological extraction database 200 may be implemented, without limitation, as a relational database, a key-value retrieval datastore such as a NOSQL database, or any other format or structure for use as a datastore that a person skilled in the art would recognize as suitable upon review of the entirety of this disclosure. One or more database tables in biological extraction database 200 may include, as a non-limiting example, a prognostic link table 300. Prognostic link table 300 may be a table relating physiological sample data as described above to prognostic labels; for instance, where an expert has entered data relating a prognostic label to a category of physiological sample data and/or to an element of physiological sample data via first graphical user interface 128 as described above, one or more rows recording such an entry may be inserted in prognostic link table 300. Alternatively or additionally, linking of prognostic labels to physiological sample data may be performed entirely in a prognostic label database as described below.

With continued reference to FIG. 3, biological extraction database 200 may include tables listing one or more samples according to sample source. For instance, and without limitation, biological extraction database 200 may include a fluid sample table 304 listing samples acquired from a person by extraction of fluids, such as without limitation blood, lymph cerebrospinal fluid, or the like. As another non-limiting example, biological extraction database 200 may include a sensor data table 308, which may list samples acquired using one or more sensor, for instance as described in further detail below. As a further non-limiting example, biological extraction database 200 may include a genetic sample table 312, which may list partial or entire sequences of genetic material. Genetic material may be extracted and amplified, as a non-limiting example, using polymerase chain reactions (PCR) or the like. As a further example, also non-limiting, biological extraction database 200 may include a medical report table 316, which may list textual descriptions of medical tests, including without limitation radiological tests or tests of strength and/or dexterity or the like. Data in medical report table may be sorted and/or categorized using a language processing module 132, for instance, translating a textual description into a numerical value and a label corresponding to a category of physiological data; this may be performed using any language processing algorithm or algorithms as referred to in this disclosure. As another non-limiting example, biological extraction database 200 may include a tissue sample table 320, which may record physiological samples obtained using tissue samples. Tables presented above are presented for exemplary purposes only; persons skilled in the art will be aware of various ways in which data may be organized in biological extraction database 200 consistently with this disclosure.

Figure 4:
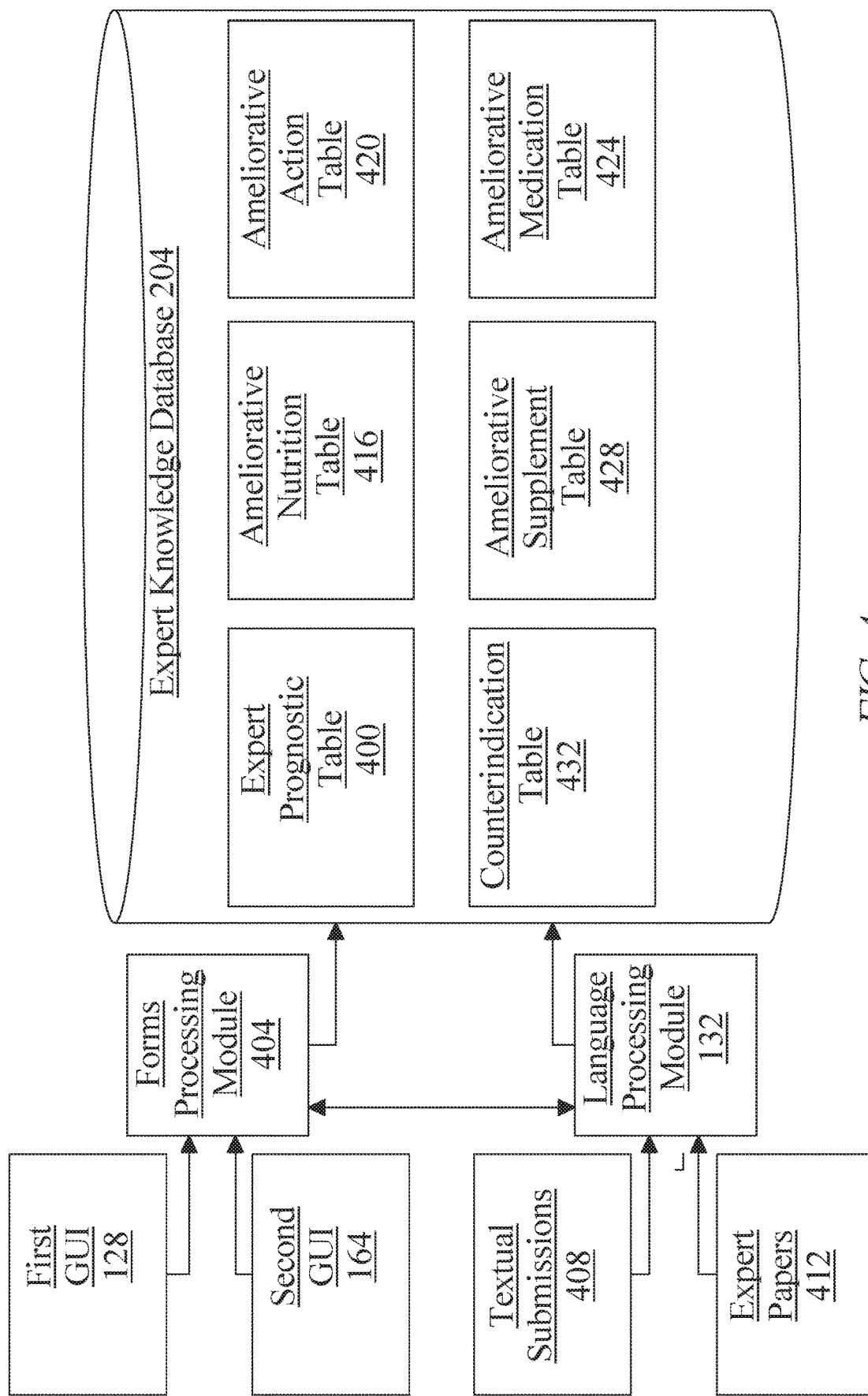
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert prognostic table 400. Expert prognostic table 400 may be a table relating physiological sample data as described above to prognostic labels; for instance, where an expert has entered data relating a prognostic label to a category of physiological sample data and/or to an element of physiological sample data via first graphical user interface 128 as described above, one or more rows recording such an entry may be inserted in expert prognostic table 400. In an embodiment, a forms processing module 404 may sort data entered in a submission via first graphical user interface 128 by, for instance, sorting data from entries in the first graphical user interface 128 to related categories of data; for instance, data entered in an entry relating in the first graphical user interface 128 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 132 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 132 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 132. Data may be extracted from expert papers 412, which may include without limitation publications in medical and/or scientific journals, by language processing module 132 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a further non-limiting example tables listing one or more ameliorative process labels; expert data populating such tables may be provided, without limitation, using any process described above, including entry of data from second graphical user interface 164 via forms processing module 404 and/or language processing module 132, processing of textual submissions 408, or processing of expert papers 412. For instance, and without limitation, an ameliorative nutrition table 416 may list one or more ameliorative processes based on nutritional instructions, and/or links of such one or more ameliorative processes to prognostic labels, as provided by experts according to any method of processing and/or entering expert data as described above. As a further example an ameliorative action table 420 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above. As an additional example, an ameliorative supplement table 424 may list one or more ameliorative processes based on nutritional supplements, such as vitamin pills or the like, and/or links of such one or more ameliorative processes to prognostic labels, as provided by experts according to any method of processing and/or entering expert data as described above. As a further non-limiting example, an ameliorative medication table 428 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above. As an additional example, a counterindication table 432 may list one or more counterindications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like. Tables presented above are presented for exemplary purposes only; persons skilled in the art will be aware of various ways in which data may be organized in expert knowledge database 204 consistently with this disclosure.

Figure 5:
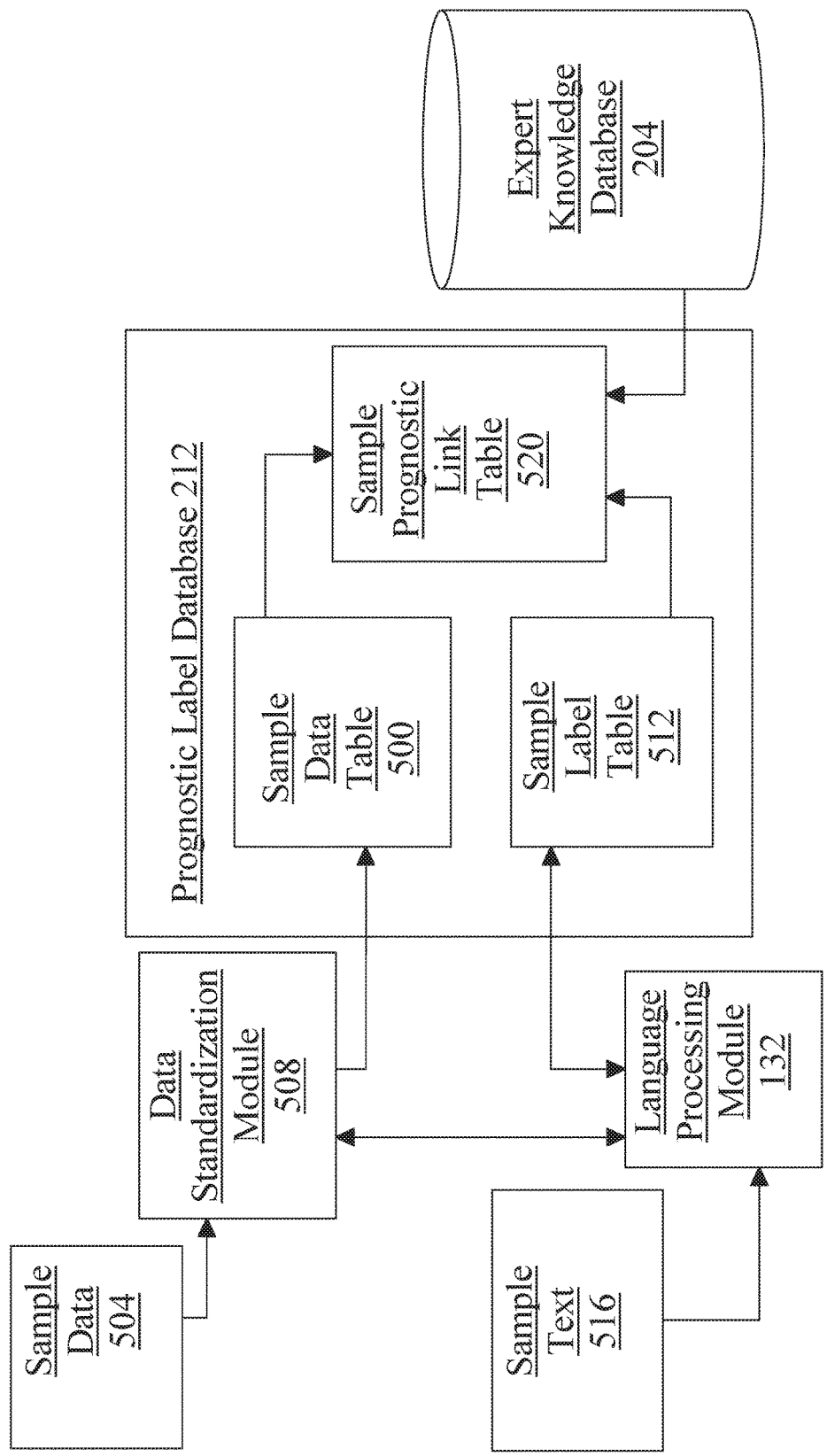
FIG. 5 is a block diagram illustrating an exemplary embodiment of a prognostic label database.

Referring now to FIG. 5, an exemplary embodiment of a prognostic label database 212 is illustrated. Prognostic label database 212 may, as a non-limiting example, organize data stored in the prognostic label database 212 according to one or more database tables. One or more database tables may be linked to one another by, for instance, common column values. For instance, a common column between two tables of prognostic label database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in prognostic label database 212 may include, as a non-limiting example, a sample data table 500. Sample data table 500 may be a table listing sample data, along with, for instance, one or more linking columns to link such data to other information stored in prognostic label database 212. In an embodiment, sample data 504 may be acquired, for instance from biological extraction database 200, in a raw or unsorted form, and may be translated into standard forms, such as standard units of measurement, labels associated with particular physiological data values, or the like; this may be accomplished using a data standardization module 508, which may perform unit conversions. Data standardization module 508 may alternatively or additionally map textual information, such as labels describing values tested for or the like, using language processing module 132 or equivalent components and/or algorithms thereto.

Continuing to refer to FIG. 5, prognostic label database 212 may include a sample label table 512; sample label table 512 may list prognostic labels received with and/or extracted from physiological samples, for instance as received in the form of sample text 516. A language processing module 132 may compare textual information so received to prognostic labels and/or form new prognostic labels according to any suitable process as described above. Sample prognostic link table may combine samples with prognostic labels, as acquired from sample label table and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Figure 6:
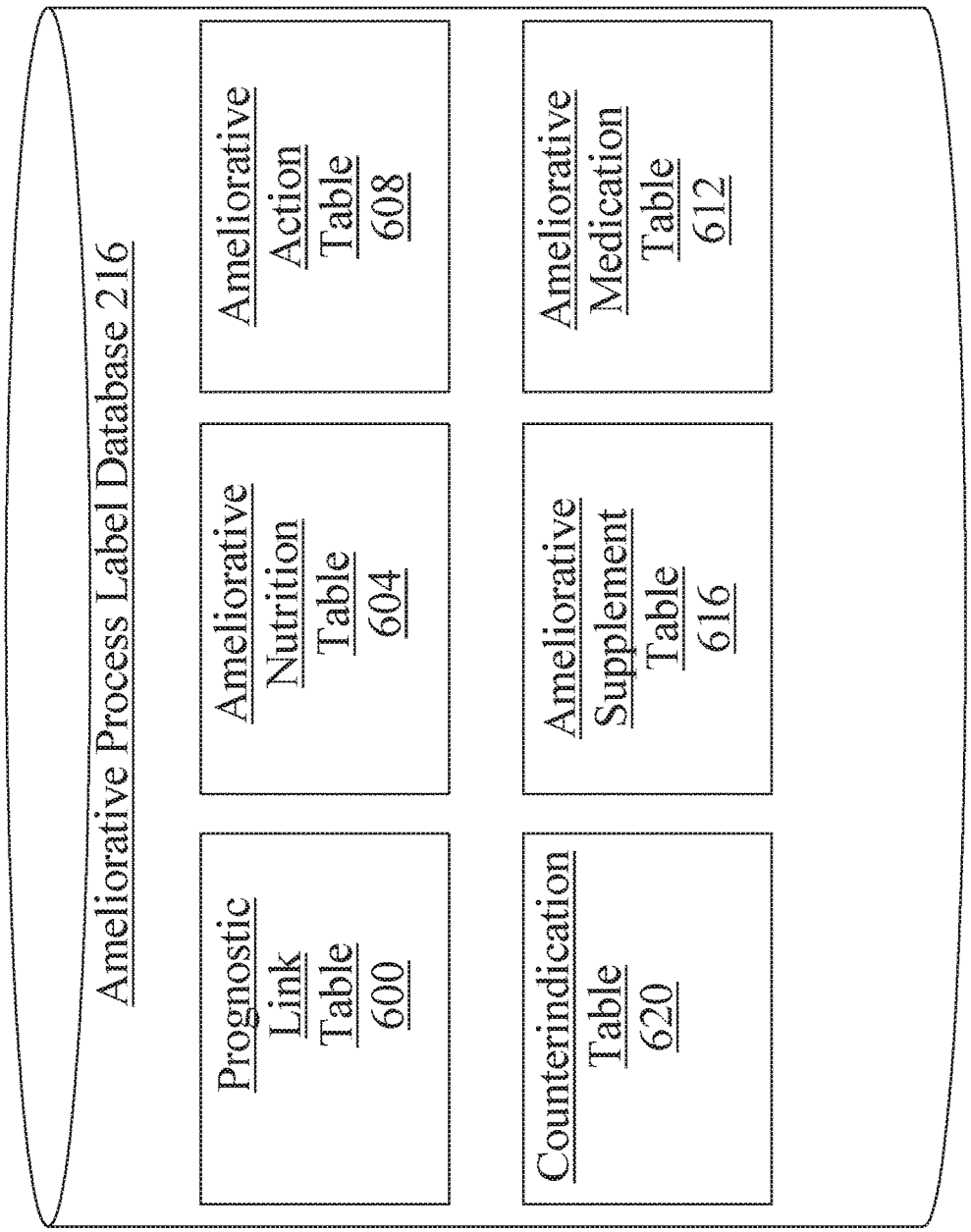
FIG. 6 is a block diagram illustrating an exemplary embodiment of an ameliorative process label database.

Referring now to FIG. 6, an exemplary embodiment of an ameliorative process label database 216 is illustrated. Ameliorative process label database 216 may, as a non-limiting example, organize data stored in the ameliorative process label database 216 according to one or more database tables. One or more database tables may be linked to one another by, for instance, common column values. For instance, a common column between two tables of ameliorative process label database 216 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, ameliorative process label database 216 may include a prognostic link table 600; prognostic link table may link ameliorative process data to prognostic label data, using any suitable method for linking data in two or more tables as described above. Ameliorative process label database 216 may include an ameliorative nutrition table 604, which may list one or more ameliorative processes based on nutritional instructions, and/or links of such one or more ameliorative processes to prognostic labels, for instance as provided by experts according to any method of processing and/or entering expert data as described above, and/or using one or more machine-learning processes as set forth in further detail below. As a further example an ameliorative action table 608 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above and/or using one or more machine-learning processes as set forth in further detail below. As an additional example, an ameliorative supplement table 612 may list one or more ameliorative processes based on nutritional supplements, such as vitamin pills or the like, and/or links of such one or more ameliorative processes to prognostic labels, as provided by experts according to any method of processing and/or entering expert data as described above and/or using one or more machine-learning processes as set forth in further detail below. As a further non-limiting example, an ameliorative medication table 616 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above and/or using one or more machine-learning processes as set forth in further detail below. As an additional example, a counter-indication table 620 may list one or more counter-indications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like; this may be acquired using expert submission as described above and/or using one or more machine-learning processes as set forth in further detail below. Tables presented above are presented for exemplary purposes only; persons skilled in the art will be aware of various ways in which data may be organized in ameliorative process database 216 consistently with this disclosure.

Figure 7:
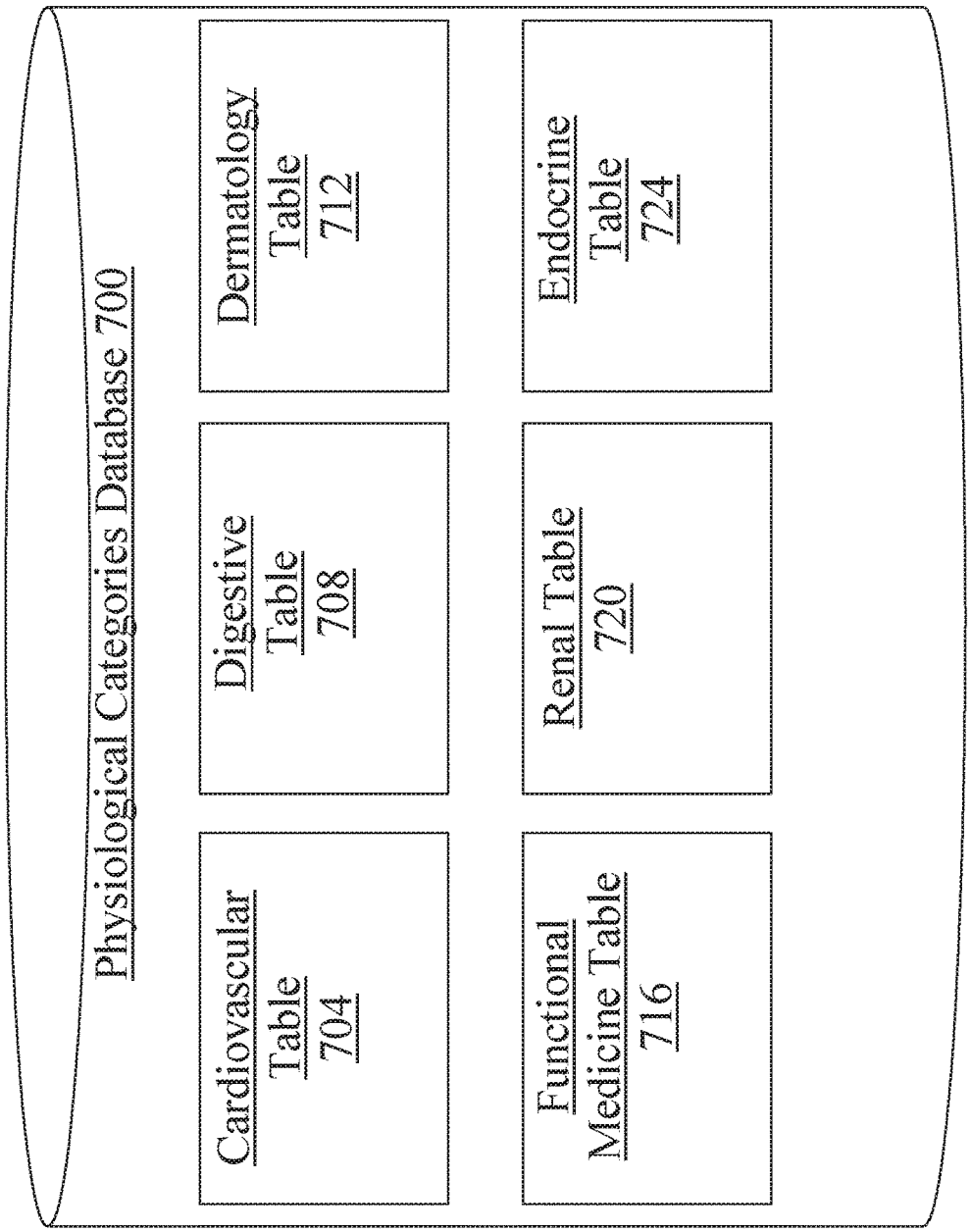
FIG. 7 is a block diagram illustrating an exemplary embodiment of a physiological categories database.

Referring now to FIG. 7, an exemplary embodiment of physiological categories database 700 is illustrated. Physiological categories database 700 may, as a non-limiting example, organize data stored in the physiological categories database 700 according to one or more database tables. One or more database tables may be linked to one another by, for instance, common column values. For instance, a common column between two tables of physiological categories database 700 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

With continued reference to FIG. 7, physiological categories database 700 include any data structure for ordered storage and retrieval of data, which may be implemented as a hardware or software module, and which may be implemented as any database structure suitable for use as biological extraction database 200. Physiological categories database 700 may include cardiovascular table 704; cardiovascular table 704 may include physiological state data 120 and/or biological extractions categorized as relating to cardiovascular system. For example, cardiovascular table 704 may include data relating to heart health such as lipid levels, troponin levels, electrocardiograms, triglycerides, myoglobin, creatine kinase, and the like. Physiological categories database 700 may include digestive table 708; digestive table 708 may include physiological state data 120 and/or biological extractions categorized as relating to digestive system. For example, digestive table 708 may include data relating to digestive health such as iron levels, ferritin levels, microbiome species within gut, *Candida Albicans* species, calprotectin levels, lactoferrin levels, neopterin levels, lysozyme levels, and the like. Physiological categories database 700 may include dermatology table 712; dermatology table 712 may include physiological state data 120 and/or biological extractions categorized as relating to dermatology. For example, dermatology table 712 may include skin biopsies, mole biopsies, immunoglobulin a (IGA) levels, cutaneous electron micrographs, immunohistochemical hybridization stains, histochemical hybridization stains, and in situ hybridization stains. Physiological categories database 700 may include functional medicine table 716; functional medicine table 716 may include physiological state data 120 and/or biological extractions categorized as relating to functional medicine. For example, functional medicine table 716 may include neurotransmitter levels, hormone levels, basal body temperature, total T4 levels, free T4 levels, free T3 levels, gut metabolic markers, digestion absorption markers, immune system hyperactivity, eosinophil protein x levels, calprotectin levels, and the like. Physiological categories database 700 may include renal table 720; renal table 720 may include physiological state data 120 and/or biological extractions categorized as relating to the renal system. For example, renal table 720 may include albumin levels, creatinine levels, glomerular filtration rate, creatinine clearance, blood urea nitrogen, urinalysis, urine protein, microalbuminuria and the like. Physiological categories database 700 may include endocrine table 724; endocrine table 724 may include physiological state data 120 and/or biological extractions categorized as relating to the endocrine system. For example, endocrine table 724 may include aldosterone levels, serum cortisol levels, hirsutism panel, adiponectin, fasting glucose level, insulin levels, hemoglobin A1C with calculated mean plasma glucose (MPG), prolactin, pituitary hormone level, and the like. In an embodiment, physiological state data 120 and/or biological extractions may be categorized to one or more tables contained within physiological categories database 700. Other tables not illustrated but which may be included in physiological categories database 700 may include for example, circulatory table, excretory table, immune table, lymphatic table, muscular table, neural table, urinary table, respiratory table, reproductive table, and the like.

Figure 8:
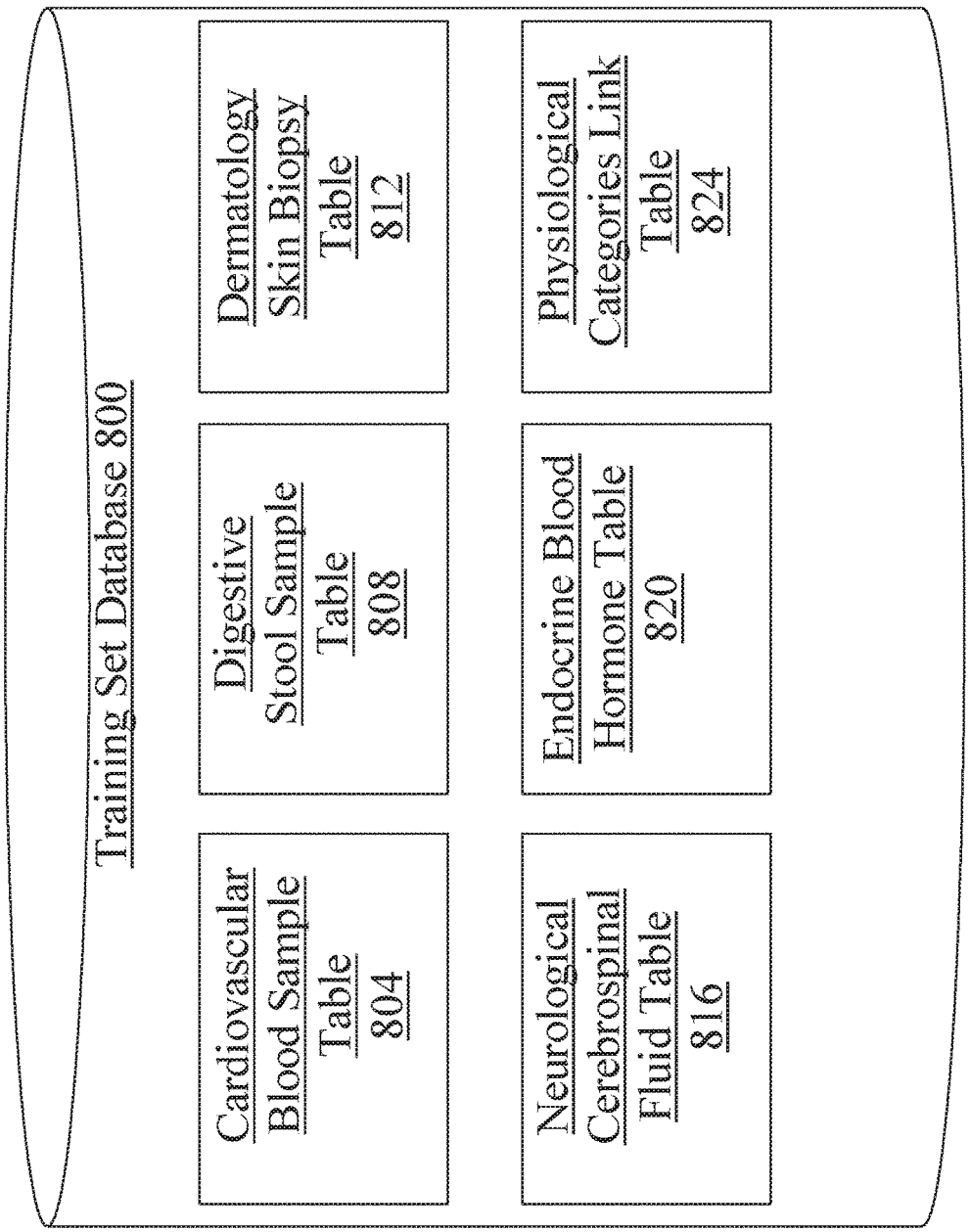
FIG. 8 is a block diagram illustrating an exemplary embodiment of a training set database.

Referring now to FIG. 8, an exemplary embodiment of training set database 800 is illustrated. Training set database 800 may, as a non-limiting example, organize data stored in the training set database 800 according to one or more database tables. One or more database tables may be linked to one another by, for instance, common column values. For instance, a common column between two tables of training set database 800 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

With continued reference to FIG. 8, training set database 800 may include any data structure for ordered storage and retrieval of data, which may be implemented as a hardware or software module, and which may be implemented as any database structure suitable for use as biological extraction database 200. Training set database 800 may include one or more tables containing training sets categorized by physiological category and sample type. Training set database 800 may include cardiovascular blood sample table 804; cardiovascular blood sample table 804 may include training sets containing physiological state data 120 categorized as relating to cardiovascular system and which include physiological data extracted from a blood sample. For example, blood sample table 804 may include training sets containing physiological state data 120 such as total cholesterol levels or total triglyceride levels. Training set database 800 may include digestive stool sample table 808; digestive stool sample table 808 may include training sets containing physiological state data 120 categorized as relating to digestive system and which include physiological data extracted from a stool sample. For example, digestive stool sample table 808 may include training sets containing physiological state data 120 such as an ova and parasite exam. Training set database 800 may include dermatology skin biopsy table 812; dermatology skin biopsy table 812 may include training sets containing physiological state data 120 categorized as relating to dermatology system and which include physiological data extracted from a skin biopsy. For example, skin biopsy table 812 may include training sets containing physiological state data 120 such as a skin sample removed from an area on the body such as the elbow or knee and the like. Training set database 800 may include neurological cerebrospinal fluid table 816; neurological cerebrospinal fluid table 816 may include training sets containing physiological state data 120 categorized as relating to neurology system and which include physiological data extracted from cerebrospinal fluid. For example, neurological cerebrospinal fluid table 816 may include for example pressure measurement, cell count, white cell differential, glucose levels, protein levels, gram stain, culture, and the like. Training set database 800 may include endocrine blood hormone table 820; endocrine blood hormone table 820 may include training sets containing physiological state data 120 categorized as relating to endocrine system and which include physiological data extracted from blood sample. For example, endocrine blood hormone table 820 may include for example estradiol levels, progesterone levels, follicle stimulating hormone, testosterone, thyroid stimulating hormone (TSH), thyroxine (T4), and the like. Training set database 800 may include physiological categories link table 824; physiological categorizes link table 824 may relate physiological state data 120 and/or biological extractions to physiological categories. For example, physiological categories link table 824 may include entries from an expert relating physiological state data 120 to a physiological category. In an embodiment, training sets contained within training set database and contained within one or more tables may include at least a data entry of a first training set 116 that includes at least an element of physiological state data 120 and at least a correlated first prognostic label. In an embodiment, first training set 116 may be correlated to a second training set 152 that includes at least a second data entry of a second training set 152 where each second data entry of the second training set 152 includes at least a second prognostic label 156 and at least a correlated ameliorative process label. In an embodiment, training sets contained within training set database 800 and/or data entries contained with each training set may be listed and contained within more than one table within training set database 800. In an embodiment, training set database 800 may include other tables not illustrated including for example cardiovascular saliva sample table, digestive blood sample table, dermatology blood sample table, neurological saliva sample, neurological amniotic sample, neurological hair sample, endocrine hair sample, and the like.

Figure 9:
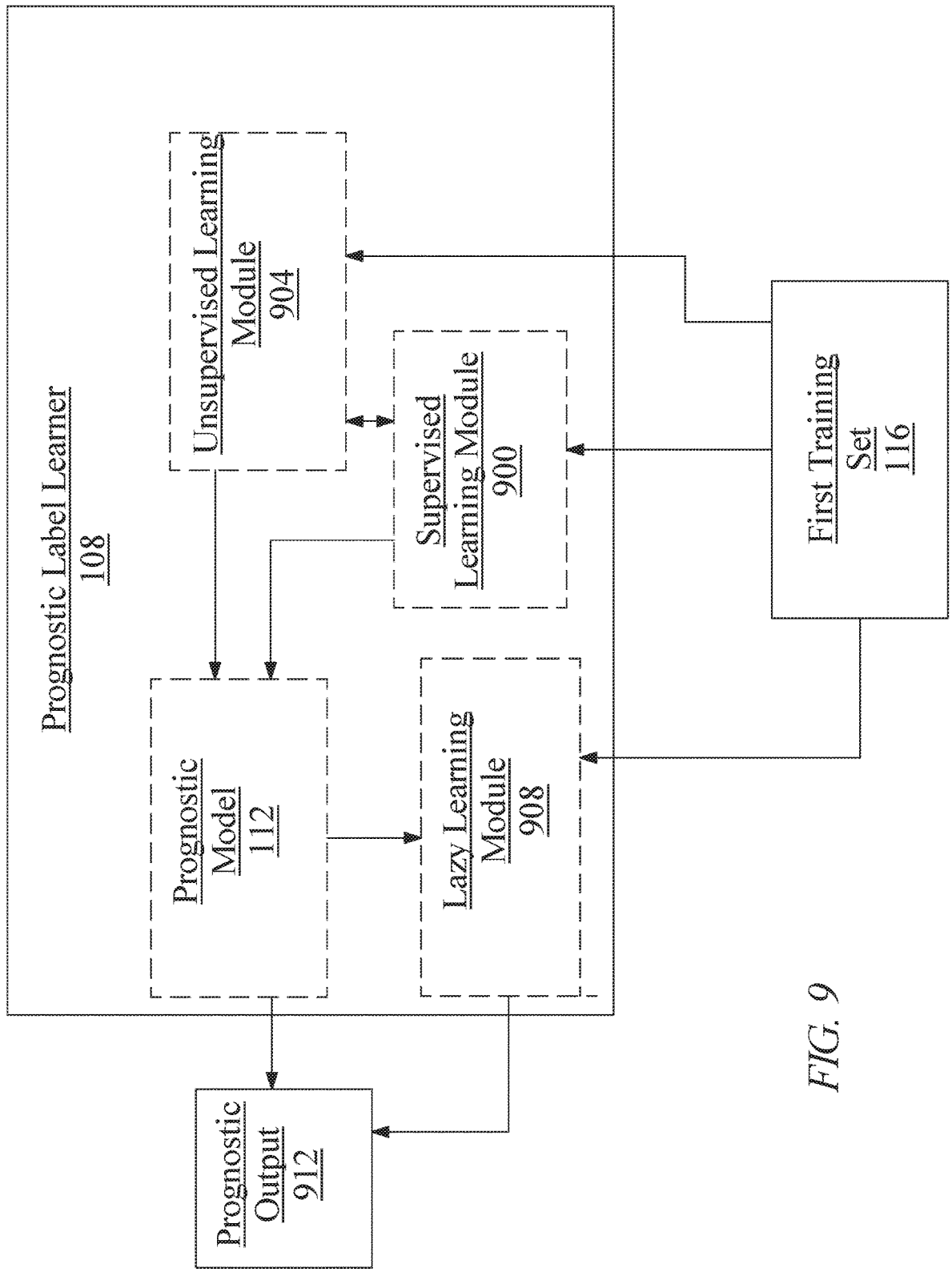
FIG. 9 is a block diagram illustrating an exemplary embodiment of a prognostic label learner.

Referring now to FIG. 9, an exemplary embodiment of prognostic label learner 108 is illustrated. Machine-learning algorithms used by prognostic label learner 108 may include supervised machine-learning algorithms, which may, as a non-limiting example be executed using a supervised learning module 900 executing on at least a server 104 and/or on another computing device in communication with at least a server 104, which may include any hardware or software module. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, prognostic labels as outputs, and a scoring function representing a desired form of relationship to be detected between elements of physiological data and prognostic labels; scoring function may, for instance, seek to maximize the probability that a given element of physiological state data 120 and/or combination of elements of physiological data is associated with a given prognostic label and/or combination of prognostic labels to minimize the probability that a given element of physiological state data 120 and/or combination of elements of physiological state data 120 is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set. Persons skilled in the art, upon reviewing the entirety of this disclosure, will be aware of various possible variations of supervised machine-learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

With continued reference to FIG. 9, machine-learning algorithms may include unsupervised processes; unsupervised processes may, as a non-limiting example, be executed by an unsupervised learning module 904 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, prognostic label learner 108 and/or at least a server 104 may perform an unsupervised machine-learning process on first training set 116, which may cluster data of first training set 116 according to detected relationships between elements of the first training set 116, including without limitation correlations of elements of physiological state data 120 to each other and correlations of prognostic labels to each other; such relations may then be combined with supervised machine-learning results to add new criteria for prognostic label learner 108 to apply in relating physiological state data 120 to prognostic labels. As a non-limiting, illustrative example, an unsupervised process may determine that a first element of physiological data acquired in a blood test correlates closely with a second element of physiological data, where the first element has been linked via supervised learning processes to a given prognostic label, but the second has not; for instance, the second element may not have been defined as an input for the supervised learning process, or may pertain to a domain outside of a domain limitation for the supervised learning process. Continuing the example a close correlation between first element of physiological state data 120 and second element of physiological state data 120 may indicate that the second element is also a good predictor for the prognostic label; second element may be included in a new supervised process to derive a relationship or may be used as a synonym or proxy for the first physiological element by prognostic label learner 108.

Still referring to FIG. 9, at least a server 104 and/or prognostic label learner 108 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to at least a server 104, prognostic label learner 108 and/or at least a server 104 may continuously or iteratively perform unsupervised machine-learning processes to detect relationships between different elements of the added and/or overall data; in an embodiment, this may enable at least a server 104 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 9, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 9, prognostic label learner 108 may alternatively or additionally be designed and configured to generate at least a prognostic output by executing a lazy learning process as a function of the first training set 116 and the at least a biological extraction; lazy learning processes may be performed by a lazy learning module 908 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover a "first guess" at a prognostic label associated with biological extraction, using first training set 116. As a non-limiting example, an initial heuristic may include a ranking of prognostic labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and prognostic labels, for instance as calculated as described above. Heuristic may include selecting some number of highest-ranking associations and/or prognostic labels. Prognostic label learner 108 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

In an embodiment, and continuing to refer to FIG. 9, prognostic label learner 108 may generate a plurality of prognostic labels having different implications for a particular person. For instance, where the at least a biological extraction includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, prognostic label learner 108 and/or at least a server 104 may perform additional processes to resolve ambiguity. Processes may include presenting multiple possible results to a medical practitioner, informing the medical practitioner that one or more follow-up tests and/or biological extractions are needed to further determine a more definite prognostic label. Alternatively or additionally, processes may include additional machine-learning steps; for instance, where reference to a model generated using supervised learning on a limited domain has produced multiple mutually exclusive results and/or multiple results that are unlikely all to be correct, or multiple different supervised machine-learning models in different domains may have identified mutually exclusive results and/or multiple results that are unlikely all to be correct. In such a situation, prognostic label learner 108 and/or at least a server 104 may operate a further algorithm to determine which of the multiple outputs is most likely to be correct; algorithm may include use of an additional supervised and/or unsupervised model. Alternatively or additionally, prognostic label learner 108 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list. Prognostic output 912 may be provided to user output device as described in further detail below.

With continued reference to FIG. 9, prognostic label learner 108 may generate a plurality of prognostic outputs each containing a ranked prognostic probability score as a function of at least a biological extraction, at least a first training set, and at least a prognostic machine-learning model. Prognostic probability score may include any of the prognostic probability scores as described above in reference to FIG. 1. In an embodiment, prognostic label learner may rank plurality of prognostic outputs in descending order of probability. In an embodiment, prognostic label learner 108 and/or at least a server may select at least a prognostic output to include in a diagnostic output as a function of prognostic probability score. For example, prognostic label learner 108 and/or at least a server may select at least a prognostic output to include in a diagnostic output having the highest prognostic probability score. For example, prognostic label learner 108 may generate a plurality of diagnostic outputs 148 for at least a biological extraction such as a skin rash whereby a first prognostic output of hives may be associated with a prognostic probability score of 92%, a second prognostic output of dermatitis may be associated with a prognostic probability score of 12%, and a third prognostic output of Leprosy may be associated with a prognostic probability score of 0.5%. In such an instance, prognostic label learner 108 may select first prognostic output of hives containing the highest prognostic probability score to be included in at least a prognostic output and/or ameliorative output.

With continued reference to FIG. 9, prognostic label learner 108 may be configured to select a prognostic machine-learning process as a function of at least a biological extraction. Selecting a prognostic machine-learning process may include selecting a machine-learning model to generate a prognostic output and/or selecting an algorithm to generate a machine-learning model. Selecting a prognostic machine-learning process may be done utilizing any of the methodologies as described above in reference to FIG. 1.

Figure 10:
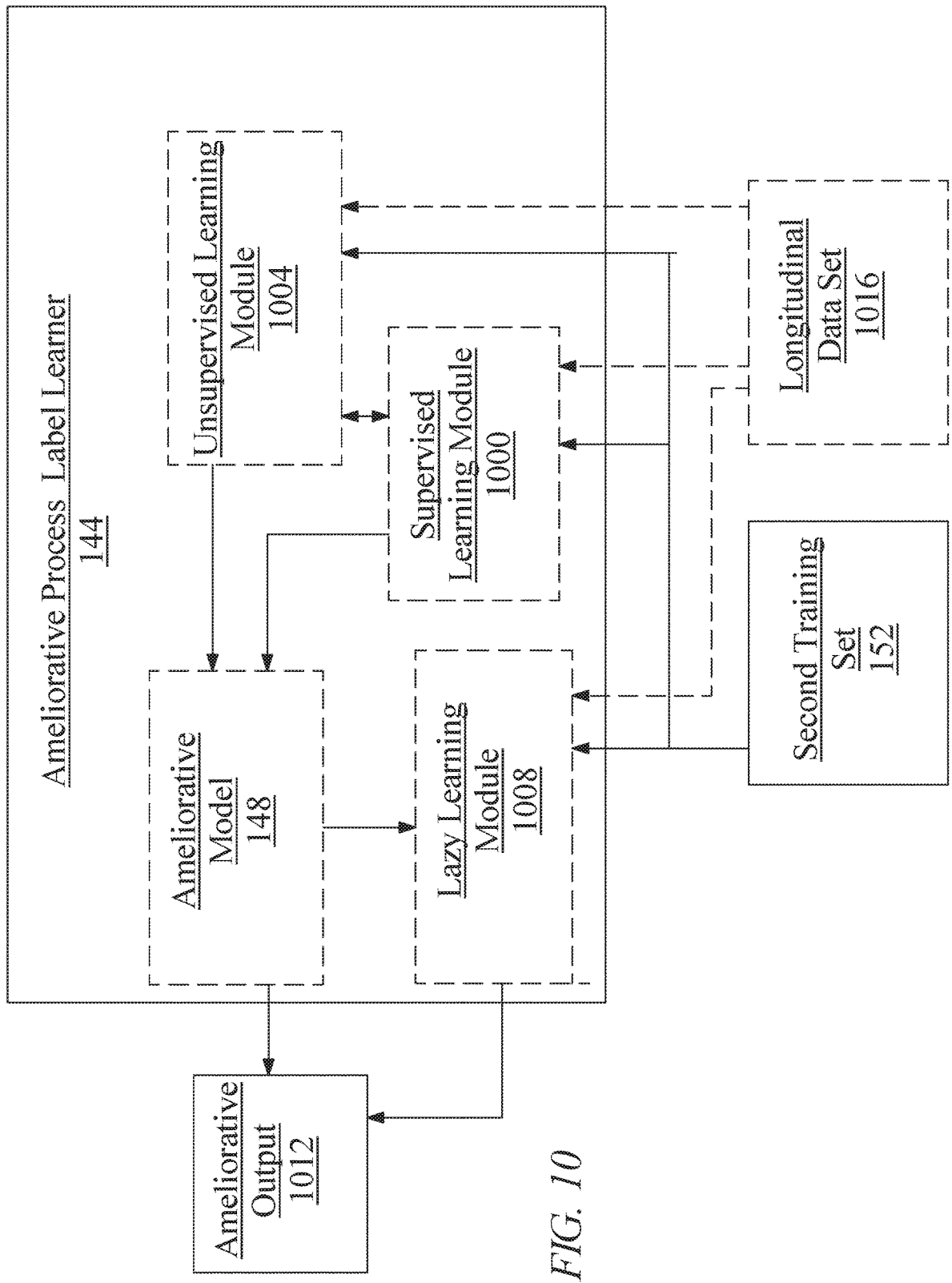
FIG. 10 is a block diagram illustrating an exemplary embodiment of an ameliorative process label learner.

Referring now to FIG. 10, an exemplary embodiment of ameliorative process label learner 144 is illustrated. Ameliorative process label learner 144 may be configured to perform one or more supervised learning processes, as described above; supervised learning processes may be performed by a supervised learning module 1000 executing on at least a server 104 and/or on another computing device in communication with at least a server 104, which may include any hardware or software module. For instance, a supervised learning algorithm may use prognostic labels as inputs, ameliorative labels as outputs, and a scoring function representing a desired form of relationship to be detected between prognostic labels and ameliorative labels; scoring function may, for instance, seek to maximize the probability that a given prognostic label and/or combination of prognostic labels is associated with a given ameliorative label and/or combination of ameliorative labels to minimize the probability that a given prognostic label and/or combination of prognostic labels is not associated with a given ameliorative label and/or combination of ameliorative labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of ameliorative labels, for instance because the ameliorative processes corresponding to the set of ameliorative labels are hypothesized or suspected to have an ameliorative effect on conditions represented by the prognostic labels, and/or are specified as linked to a medical specialty and/or field of medicine covering a particular set of prognostic labels and/or ameliorative labels. As a non-limiting example, a particular set prognostic labels corresponding to a set of cardiovascular conditions may be typically treated by cardiologists, and a supervised machine-learning process may be performed to relate those prognostic labels to ameliorative labels associated with various treatment options, medications, and/or lifestyle changes.

With continued reference to FIG. 10, ameliorative process label learner 144 may perform one or more unsupervised machine-learning processes as described above; unsupervised processes may be performed by an unsupervised learning module 1004 executing on at least a server 104 and/or on another computing device in communication with at least a server 104, which may include any hardware or software module. For instance, and without limitation, ameliorative process label learner 144 and/or at least a server 104 may perform an unsupervised machine-learning process on second training set 152, which may cluster data of second training set 152 according to detected relationships between elements of the second training set 152, including without limitation correlations of prognostic labels to each other and correlations of ameliorative labels to each other; such relations may then be combined with supervised machine-learning results to add new criteria for ameliorative process label learner 144 to apply in relating prognostic labels to ameliorative labels. As a non-limiting, illustrative example, an unsupervised process may determine that a first prognostic label 124 correlates closely with a second prognostic label 156, where the first prognostic label 124 has been linked via supervised learning processes to a given ameliorative label, but the second has not; for instance, the second prognostic label 156 may not have been defined as an input for the supervised learning process, or may pertain to a domain outside of a domain limitation for the supervised learning process. Continuing the example, a close correlation between first prognostic label 124 and second prognostic label 156 may indicate that the second prognostic label 156 is also a good match for the ameliorative label; second prognostic label 156 may be included in a new supervised process to derive a relationship or may be used as a synonym or proxy for the first prognostic label 124 by ameliorative process label learner 144. Unsupervised processes performed by ameliorative process label learner 144 may be subjected to any domain limitations suitable for unsupervised processes performed by prognostic label learner 108 as described above.

Still referring to FIG. 10, at least a server 104 and/or ameliorative process label learner 144 may detect further significant categories of prognostic labels, relationships of such categories to ameliorative labels, and/or categories of ameliorative labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to at least a server 104, ameliorative process label learner 144 and/or at least a server 104 may continuously or iteratively perform unsupervised machine-learning processes to detect relationships between different elements of the added and/or overall data; in an embodiment, this may enable at least a server 104 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

Continuing to view FIG. 10, ameliorative process label learner 144 may be configured to perform a lazy learning process as a function of the second training set 152 and the at least a prognostic output to produce the at least an ameliorative output; a lazy learning process may include any lazy learning process as described above regarding prognostic label learner 108. Lazy learning processes may be performed by a lazy learning module 1008 executing on at least a server 104 and/or on another computing device in communication with at least a server 104, which may include any hardware or software module. Ameliorative output 1012 may be provided to a user client device 140 and/or an advisor client device 136 as described in further detail below.

In an embodiment, and still referring to FIG. 10, ameliorative process label learner 144 may generate a plurality of ameliorative labels having different implications for a particular person. For instance, where a prognostic label indicates that a person has a magnesium deficiency, various dietary choices may be generated as ameliorative labels associated with correcting the deficiency, such as ameliorative labels associated with consumption of almonds, spinach, and/or dark chocolate, as well as ameliorative labels associated with consumption of magnesium supplements. In such a situation, ameliorative process label learner 144 and/or at least a server 104 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine-learning steps. For instance, ameliorative process label learner 144 may perform one or more lazy learning processes using a more comprehensive set of user data to identify a more probably correct result of the multiple results. Results may be presented and/or retained with rankings, for instance to advise a medical professional of the relative probabilities of various ameliorative labels being correct or ideal choices for a given person; alternatively or additionally, ameliorative labels associated with a probability of success or suitability below a given threshold and/or ameliorative labels contradicting results of the additional process, may be eliminated. As a non-limiting example, an additional process may reveal that a person is allergic to tree nuts, and consumption of almonds may be eliminated as an ameliorative label to be presented.

Continuing to refer to FIG. 10, ameliorative process label learner 144 may be designed and configured to generate further training data and/or to generate outputs using longitudinal data 1016. As used herein, longitudinal data 1016 may include a temporally ordered series of data concerning the same person, or the same cohort of persons; for instance, longitudinal data 1016 may describe a series of blood samples taken one day or one month apart over the course of a year. Longitudinal data 1016 may related to a series of samples tracking response of one or more elements of physiological data recorded regarding a person undergoing one or more ameliorative processes linked to one or more ameliorative process labels. Ameliorative process label learner 144 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given ameliorative process over time on a physiological parameter. Functions may be compared to each other to rank ameliorative processes; for instance, an ameliorative process associated with a steeper slope in curve representing improvement in a physiological data element, and/or a shallower slope in a curve representing a slower decline, may be ranked higher than an ameliorative process associated with a less steep slope for an improvement curve or a steeper slope for a curve marking a decline. Ameliorative processes associated with a curve and/or terminal data point representing a value that does not associate with a previously detected prognostic label may be ranked higher than one that is not so associated. Information obtained by analysis of longitudinal data 1116 may be added to ameliorative process database and/or second training set.

With continued reference to FIG. 10, ameliorative process label learner 144 may be configured to generate a plurality of ameliorative outputs each containing a short-term indicator and a long-term indicator. Prognostic improvement score includes any of the prognostic improvement scores as described above in reference to FIG. 1. In an embodiment, ameliorative process label learner 144 may rank plurality of ameliorative outputs in descending order of short-term indicator and/or long-term indicator. For instance and without limitation, ameliorative process label learner 144 may generate a plurality of ameliorative outputs for a prognostic output such as hypertension ranked by short-term indicators which may include a first ameliorative output such as a ubiquinol supplementation containing a short-term indicator that includes a 87% chance of reducing systolic blood pressure by 10 mmHg, a second ameliorative output such as a high blood pressure medication containing a short-term indicator containing a 82% chance of reducing systolic blood pressure by 7 mmHg, and a third ameliorative output such as a yoga meditation sequence containing a short-term indicator containing a 12% chance of reducing systolic blood pressure by 5 mmHg. In an embodiment, ameliorative process label learner 144 may select at least an ameliorative process label containing the highest prognostic improvement score. In yet another non-limiting example, ameliorative process label learner 144 may rank plurality of ameliorative outputs in descending order of long-term indicator. For instance and without limitation, ameliorative process label leaner 144 may generate a plurality of ameliorative outputs for a prognostic output such as hypertension ranked by long-term indicators which may include a first ameliorative output such as a high blood pressure medication containing a long-term indicator containing a 74% chance of developing a cough, a second ameliorative output such as a yoga meditation sequence containing a long-term indicator containing a 68% chance of increasing flexibility, and a third ameliorative output such as ubiquinol supplementation containing a long-term indicator that includes a 2% chance of dry eye. In an embodiment, ameliorative process label learner 144 may evaluate short-term and long-term indicators to determine whether they offer a positive and/or negative benefit and weigh possibilities between short-term and long-term risks and benefits. For instance in the above example, ranking of short-term indicators and long-term indictors and evaluation of positive and/or negative benefit afforded may cause yoga to be selected by ameliorative process label learner 144 even thought it was ranked last for short-term indicator because it is associated with a positive overall long-term benefit whereas an ameliorative output such as blood pressure medication is associated with the highest long-term indicator risk of developing a cough. In an embodiment, ameliorative process label learner 144 may evaluate and weigh risks and/or benefits of short-term indicator and long-term indicator of a given ameliorative output. For example, in the above hypertension example, ameliorative process label learner 144 may weigh long-term indicator risk of cough associated with an ameliorative output of blood pressure medication versus short-term indicator of a 82% chance of a reduction of blood pressure by 7 mmHg for an individual who may need immediate short-term lowering of blood pressure such as an individual recovering from an acute myocardial infarction where blood pressure needs to be immediately lowered acutely to reduce the risk of a second myocardial infarction from presenting.

With continued reference to FIG. 10, ameliorative process label learner 144 may be configured to select an ameliorative machine-learning process as a function of a prognostic label. This may include for example selecting a machine-learning model and/or selecting an algorithm to generate a machine-learning model. This may be done utilizing any of the methodologies as described above in reference to FIG. 1.

Figure 11:
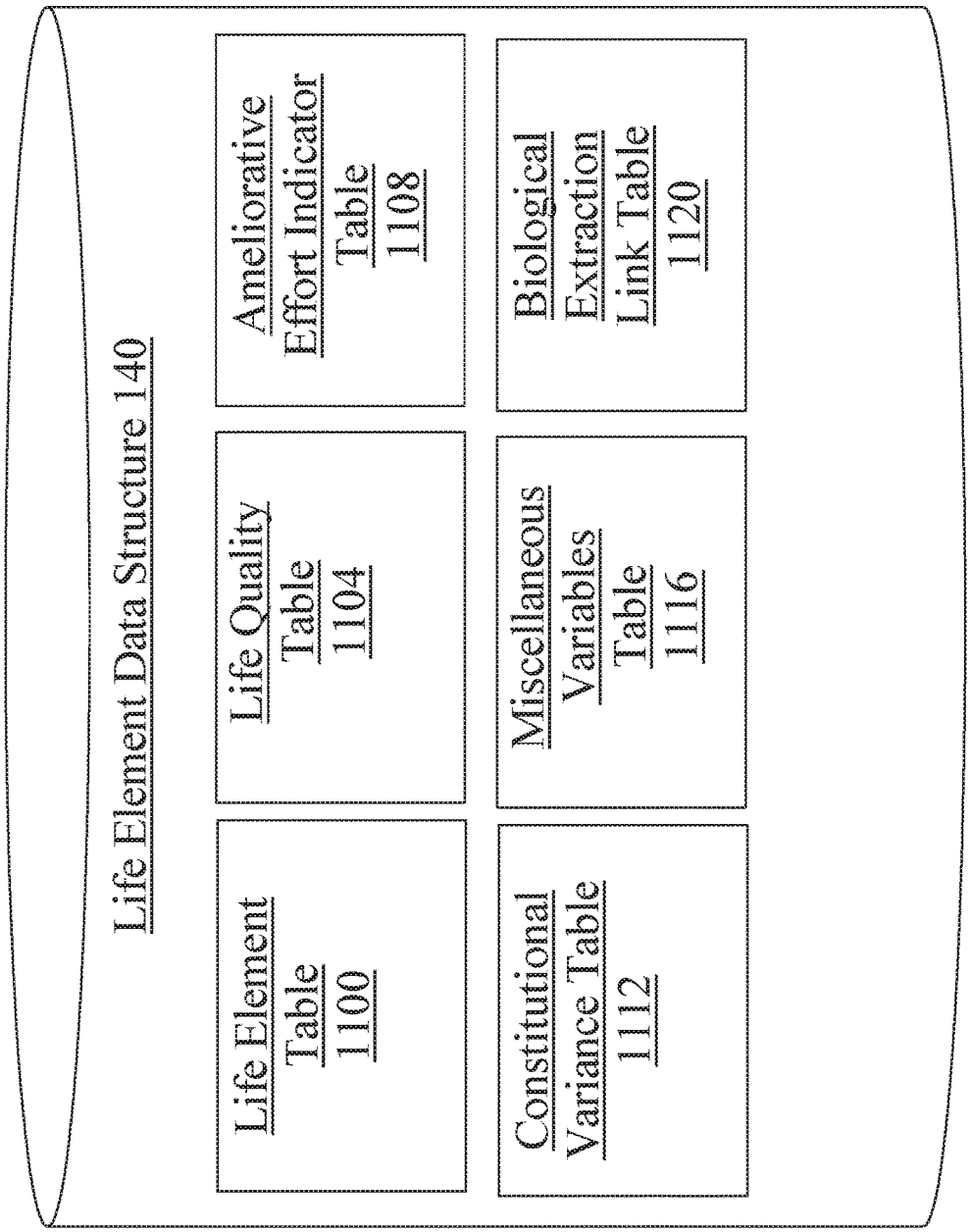
FIG. 11 is a block diagram illustrating an exemplary embodiment of a life element data structure.

Referring now to FIG. 11, an exemplary embodiment of life element data structure 176 is illustrated. In an embodiment, life element data structure 176 may, as a non-limiting example, organize data stored in life element data structure 176 according to one or more database tables. One or more database tables may be linked to one another by, for instance, common column values. For instance, a common column between two tables of life element data structure 176 may include an identifier of entries received from a particular user containing a series of repeated user entries. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

With continued reference to FIG. 11, life element data structure 176 may include any data structure for ordered storage and retrieval of data, which may be implemented as a hardware or software module, and which may be implemented as any database structure suitable for use as biological extraction database 200. Life element data structure 176 may include one or more tables containing one or more user life element datums that may include user specific and user entered information that may be utilized by loss function module 180 to generate a loss function and minimize the loss function. Life element data structure 176 may contain one or more tables containing user entries that may be utilized as variables when generating a loss function. Life element data structure 176 may include life element table 1100; life element table 1100 may include one or more user entries regarding life element variables. For example, life element table 1100 may include an entry containing a datum describing a user's preference for a goal user aspires to achieve such as to reduce the number of migraines user experiences each month. Life element data structure 176 may include life quality table 1104; life quality table 1104 may include one or more user entries regarding life quality variables. For example, life quality table 1104 may include a user's preference to utilize oral medications first before intravenous meditations. Life element data structure 176 may include ameliorative effort indicator table 1108; ameliorative effort indicator table 1108 may include one or more user entries regarding ameliorative effort indicator variables. For example, ameliorative effort indicator table 1108 may include a user's preference to spend three hours each week preparing home cooked meals. Life element data structure 176 may include constitutional variance table 1112; constitutional variance table 1112 may include one or more user entries regarding constitutional variance variables. For example, constitutional variance table 1112 may include a user's long-term longevity goal to reduce the number of hypoglycemic episodes a user experiences in half. Life element data structure 176 may include miscellaneous variables table 1116; miscellaneous variables table 1116 may include one or more user entries regarding miscellaneous variables. For example, miscellaneous variables may include a description of one or more short-term and/or long-term stressors that a user experiences, or a description of one or more short-term longevity goals. Life element data structure 176 may include biological extraction link table 1120; biological extraction link table 1120 may link one or more biological extractions contained within biological extraction database 200 to one or more variables contained within life element data structure 176. Life element data structure 176 may include one or more additional tables not pictured, which may include for example a prognostic link table which may link one or more prognostic outputs to one or more variables contained within life element data structure 176.

Figure 12:
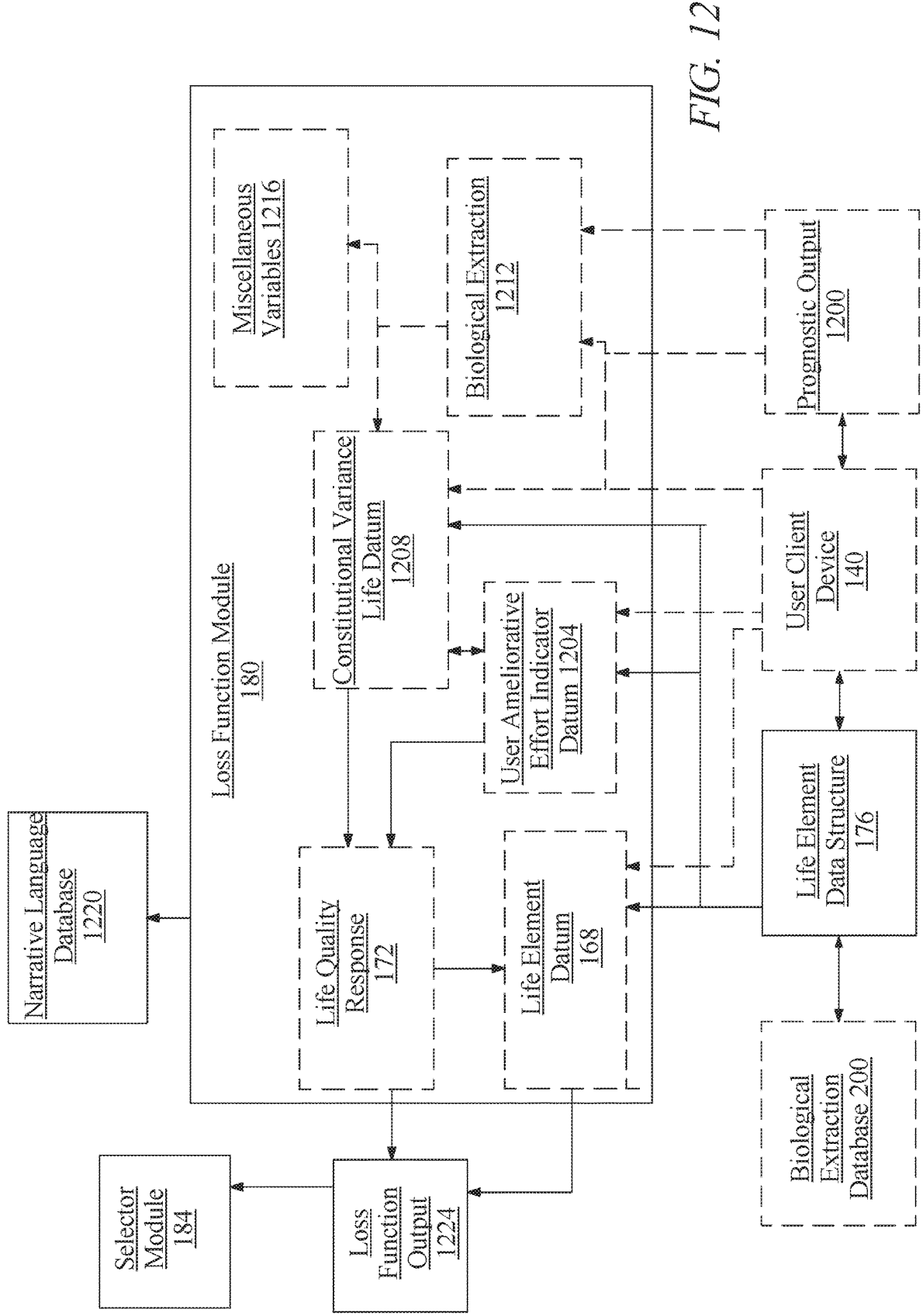
FIG. 12 is a block diagram illustrating an exemplary embodiment of a loss function module.

Referring now to FIG. 12, an exemplary embodiment of loss function module 180 is illustrated. Loss function module 180 may be implemented as a hardware or software module. Loss function module 180 is configured to generate a plurality of ameliorative outputs, the plurality of ameliorative outputs associated with a plurality of short-term indicators and a plurality of long-term indicators, as a function of the at least a prognostic output wherein each ameliorative output of the plurality of ameliorative outputs includes at least a short-term indicator of the plurality of short-term indicators and at least a long-term indicator of the plurality of long-term indicators. Loss function may include any of the loss functions as described above. Loss function module 180 may perform algorithms that may include weighted variables that may be customized to a user. Loss function module 180 may generate algorithms that may minimize distance between variables and may seek to diminish the loss function. Loss function algorithms may utilize weighted variables customized to each user. For example, user entries that contain trends and patterns as to ameliorative outputs may be utilized to select ameliorative outputs based on trends and patterns. Variables utilized to generate loss function generated by loss function module 180 include any of the variables described above in reference to FIG. 11 and contained within life element data structure 176.

With continued reference to FIG. 12, loss function module 180 generates a loss function as a function of the plurality of short-term indicators and the plurality of long-term indicators using at least a user life element datum. Loss function module 180 may receive at least a prognostic output 1200 from at least a server 104, from a user-client device 140, advisor client device 136, and/or from another device connected to and/or operating in combination with system 100. In an embodiment, at least a server 104 may generate prognostic output 1200 by prognostic label learner 108 as described above in more detail in reference to FIG. 1. Variables utilized to generate loss function by loss function module 180 may be stored in life element data structure 176. Life element data structure 176 may include any of the life element data structure 176 as described above. For example, life element data structure 176 may include a variable such as life element datum 168 which may include a goal that a user seeks to achieve such as a goal to lose twelve pounds or a goal to cook five meals each week at home. Life element data structure 176 may include a life quality response 172 which may include any of the life quality responses 172 as described above. For example, life quality response 172 may include a variable relating to a user's decision to receive treatment for an incurable condition or a user's decision to refuse a particular treatment for religious reasons such as a member of the Amish faith who may refuse a heart transplant. Life element data structure 176 may include entries regarding other variables that may be utilized to generate loss function, including user ameliorative effort indicator datum 1204. User ameliorative effort indicator datum 1204 may include a variable that includes a user response indicating how much time, energy, and/or resources a user may be willing to devote to a particular ameliorative output as described above in more detail. For example, user ameliorative effort indicator datum 1204 may include an entry describing how much time each week a user may seek to spend on a particular ameliorative treatment such as if a user will exercise for three hours each week or a user will devote one hour each week to shopping for fresh ingredients to prepare meals with. Life element data structure 176 may include variables pertaining to constitutional variance life datum 1208. Constitutional variance life datum 1208 may include any of the constitutional variance life datums as described above. Constitutional variance life datum 1208 may include a variable that includes a user's long-term longevity goal such as a desire to become more flexible, or to better control and reduce the number of hypoglycemic attacks that a user experiences each month. Loss function module 180 may utilize life element datums that include biological extractions 1212 that may be utilized as variables to generate loss function. Biological extraction 1212 may include any of the biological extractions as described above in reference to FIG. 1. Biological extractions 1212 may be received from biological extraction database 200. Loss function module 180 may generate loss function from miscellaneous variables 1216 which may include any of the miscellaneous variables as described above in reference to FIG. 11. Loss function module 180 may include narrative language database 1220. Narrative language database may contain one or more tables associating one or more biological extractions, one or more life element datums, one or more prognostic outputs, one or more ameliorative outputs, and the like into narrative language as described in more detail below. Loss function module 180 may generate a loss function output which may include a plurality of ameliorative outputs 1224 ranked as a function of minimizing the loss function. Ranking may include a ranking in decreasing order of preference as a function of minimizing a loss function of user-specific variables and entries. Loss function output may be transmitted to selector module 184 which may utilize loss function output in combination with other entries to select at least an ameliorative output.

Figure 13:
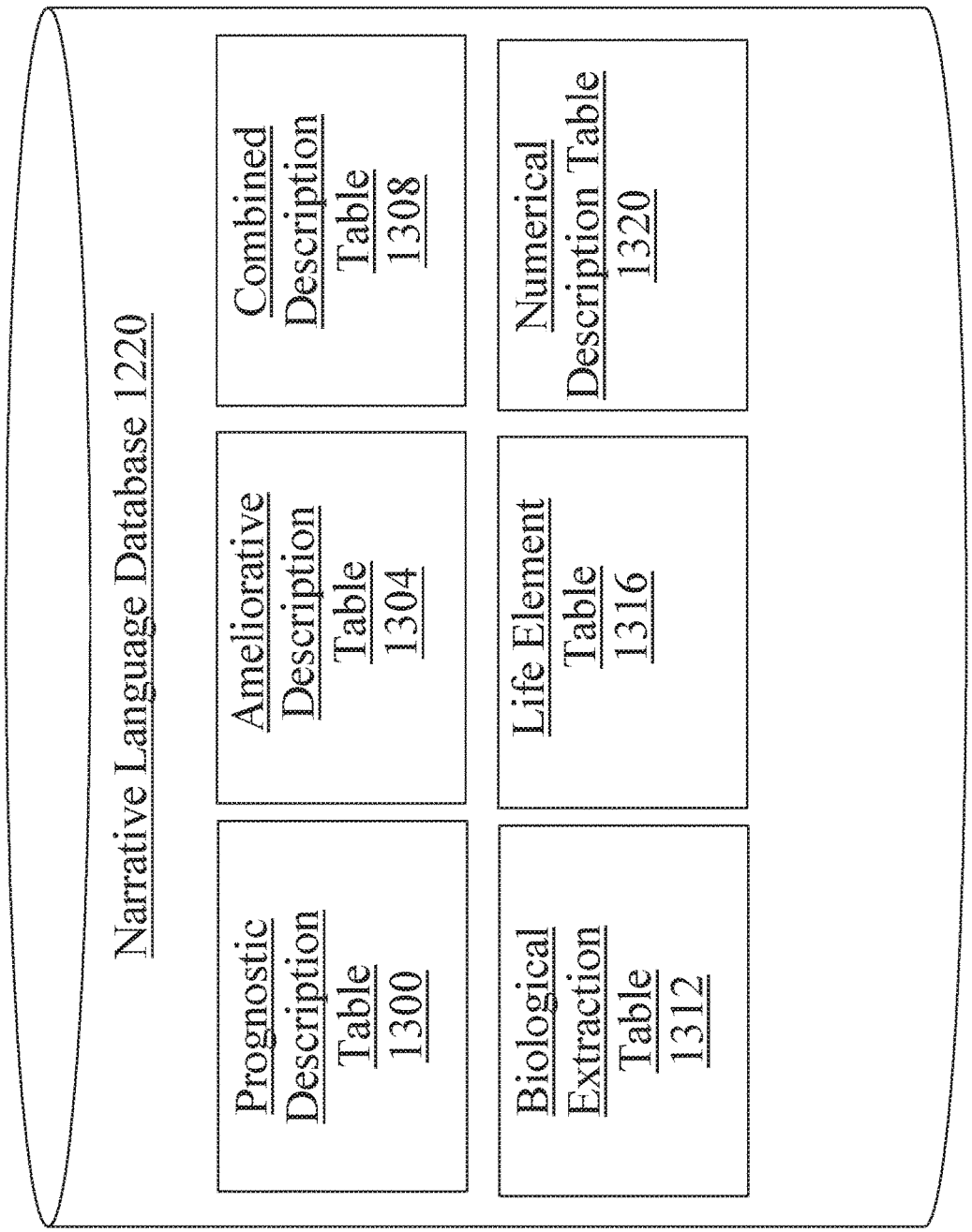
FIG. 13 is a block diagram illustrating an exemplary embodiment of a narrative language database.

Referring now to FIG. 13, an exemplary embodiment of narrative language database is illustrated. Narrative language database 1220 may be implemented as any database and/or datastore suitable for use as biological extraction database 200 as described above. One or more database tables in narrative language database 1220 may include, without limitation, a prognostic description table 1300, which may link prognostic labels to narrative descriptions associated with prognostic labels. One or more database tables in narrative language database 1220 may include, without limitation, an ameliorative description table 1304, which may link ameliorative process labels to narrative descriptions associated with ameliorative process labels. One or more database tables in narrative language database 1220 may include, without limitation, a combined description table 1308, which may link combinations of prognostic labels and ameliorative labels to narrative descriptions associated with the combinations. One or more database tables in narrative language database 1220 may include, without limitation, a biological extraction table 1312, which may link one or more biological extractions to narrative descriptions associated with one or more biological extractions. One or more database tables in narrative language database 1220 may include, without limitation, life element table 1316, which may link training sets to narrative descriptions associated with training sets, such as physiological state data 120 used in a training set. One or more database tables in narrative language database 1220 may include, without limitation, numerical description table 1320, which may link numerical outputs such as ameliorative output rankings to narrative descriptions associated with those narrative descriptions. Tables in narrative language database 1220 may be populated, as a non-limiting example, using submissions from experts, which may be collected according to any processes described above. Persons skilled in the art, upon reviewing the entirety of this disclosure, will be aware of various ways in which entries in narrative language database 1220 may be categorized and/or organized.

Figure 14:
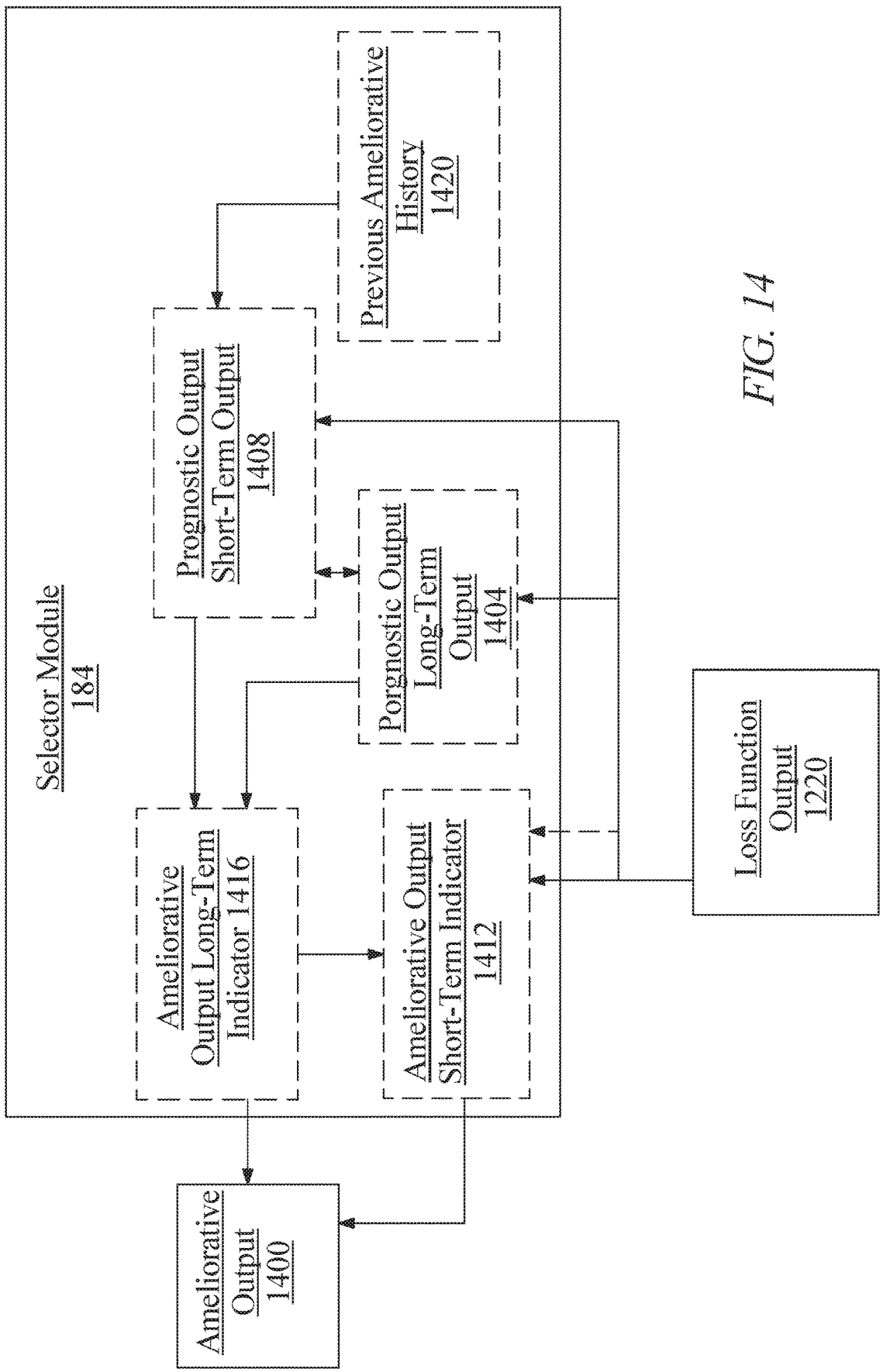
FIG. 14 is a block diagram illustrating an exemplary embodiment of a selector module.

Referring now to FIG. 14, an exemplary embodiment of selector module 184 is illustrated. Loss function module 180 may be implemented as a hardware or software module. Selector module 184 may be designed and configured to select at least an ameliorative output 1400 from the plurality of ameliorative outputs as a function of minimizing a loss function. Selector module 184 may utilize loss function output and other inputs to select at least an ameliorative output 1400. Loss function output may include any of the loss function outputs as described above. Selector module 184 may weigh and examine prognostic output long-term output 1404 which may include any of the prognostic output long-term outputs as described above. For example, a prognostic output such as a systemic *Candida Albicans* overgrowth may include a long-term output that includes eradication of *Candida Albicans* from the body. Selector module 184 may weigh and examine prognostic output short-term output 1408 which may include any of the prognostic output short-term outputs as described above. For example, prognostic output such as a systemic *Candida Albicans* overgrowth may include a short-term output that includes reducing user symptom of itching, gas, and bloating. In addition to prognostic long-term and short-term outputs, selector module 184 may weigh and examine ameliorative outputs contained within loss function output. In an embodiment, loss function output may include ameliorative outputs ranked in descending order of selection as a function of minimizing a loss function by loss function module 180 and selecting an ameliorative output as a function of minimizing the loss function in combination with a prognostic output and life element datums as described above in more detail in reference to FIG. 12. Selector module 184 may weigh and examine ameliorative output short-term indicator 1412 of an ameliorative output contained within loss function output. For example, loss function output 1220 containing two ameliorative outputs, a first ameliorative output with an ameliorative output short-term indictor that includes eradication of *Candida*, and a second ameliorative output with an ameliorative output short-term indicator that includes eradication of *Candida* and *Clostridium Difficile* may be utilized by selector module 184 to select second ameliorative output based on getting double the action to eradicate both *Candida* and *Clostridium Difficile* with only one ameliorative output. Ameliorative output short-term indicator may be balanced by selector module 184 against ameliorative output long-term indicator 1416. For example, loss function output 1220 containing two ameliorative outputs with ameliorative output short-term indicator as described above may be utilized in combination with ameliorative output long-term indicator 1416 to select an ameliorative output. For example, the first ameliorative output that includes short-term indicator that includes eradication of *Candida* may contain a long-term indicator 1416 that includes elimination of beneficial bacteria in the gastrointestinal tract. Second ameliorative output that includes short-term indicator that includes eradication of *Candida* and *Clostridium Difficile* may include long-term indicator 1416 that includes elimination of beneficial bacteria in the gastrointestinal tract in addition to long term complications that include gas, diarrhea, and bloating. Selector module 184 may also balance previous ameliorative history 1420 which may include a description of a previous ameliorative treatment, therapy, and/or possible ameliorative output that a user tried and/or utilized in the past that may influence selection of an ameliorative output. For example, a user with a previous ameliorative history that includes a topical cream that was utilized by a user to eradicate a topical skin rash of *Candida* may be utilized in selecting an ameliorative output contained within loss function output to select a topical cream if contained within loss function output. Selector module 184 may balance and utilize above described factors to balance and select ameliorative output 1400. In an embodiment, selector module 184 may be configured to generate a second loss function utilizing loss function outputs and above described factors to generate ameliorative output. Selector module 184 may select ameliorative output 1400 by ranking ameliorative outputs as a function of ameliorative long-term indicator 1416 and select at least an ameliorative output 1400 as a function of the ameliorative long-term indicator 1416.

Figure 15:
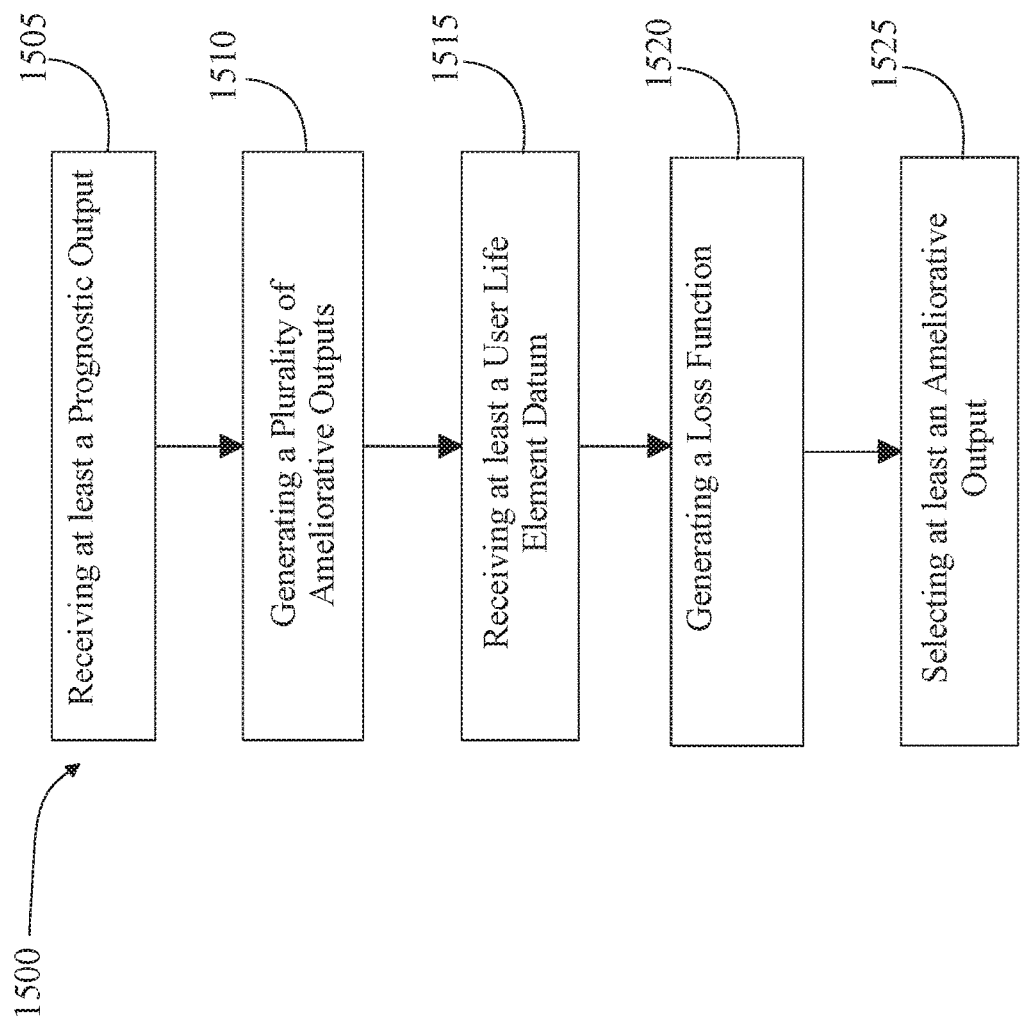
FIG. 15 is a process flow diagram illustrating an exemplary embodiment of a method for selecting an ameliorative output using artificial intelligence.

Referring now to FIG. 15, an exemplary embodiment of a method of selecting an ameliorative output using artificial intelligence is illustrated. At step 1505 at least a server receives at least a prognostic output wherein the at least a prognostic output includes at least a short-term output and at least a long-term output. Prognostic output may include any of the prognostic outputs as described above in reference to FIGS. 1-15. Prognostic output may be received from advisor client device, user client device, and/or any other device connected or in communication with system 100. In an embodiment, system 100 may be utilized to generate prognostic output utilizing prognostic label learner as described above in more detail in reference to FIG. 1. Generating prognostic output may include receiving at least a biological extraction from a user, selecting at least a training set as a function of the at least a biological extraction, and generating a machine-learning process as a function of the at least a biological extraction and the at least a training set. This may be done utilizing any of the methodologies as described above in reference to FIGS. 1-15. Receiving at least a prognostic output includes at least a short-term output and at least a long-term output. Short-term output may include any of the short-term outputs as described above in reference to FIGS. 1-15. Long-term output may include any of the long-term outputs as described above in reference to FIGS. 1-15. For example, prognostic output such as high cholesterol may include a short-term output that includes a reduction in total cholesterol and a long-term output that includes a reduction in risk for developing heart disease. In yet another non-limiting example, prognostic output such as cancer may include a short-term output that includes eliminating cancer cell from the body and a long-term output that includes minimizing side-effects of cancer treatment. In yet another non-limiting example prognostic output such as epilepsy may include a short-term output that includes reducing the number of epileptic attacks and a long-term output that includes eliminating epileptic attacks.

With continued reference to FIG. 15, at step 1510 at least a server generates a plurality of ameliorative outputs the plurality of ameliorative outputs associated with a plurality of short-term indicators and a plurality of long-term indicators as a function of at least a prognostic output wherein each ameliorative output of the plurality of ameliorative outputs includes at least a short-term indicator of the plurality of short-term indicators and at least a long-term indicator of the plurality of long-term indicators. Generating a plurality of ameliorative outputs includes selecting at least a training set as a function of at least a prognostic output and generating a machine-learning process as a function of the at least a prognostic output and the at least a training set. Generating a plurality of ameliorative outputs may be done by ameliorative process label learner as described above in reference to FIG. 1 and FIG. 10. Ameliorative process label learner may be configured to generate a machine-learning process including any of the machine-learning processes as described above in reference to FIG. 1 and FIG. 10. For example, ameliorative process label learner may generate a machine-learning process that includes a supervised learning algorithm or an unsupervised learning algorithm. Plurality of ameliorative outputs include at least a short-term indicator and at least a long-term indicator. Short-term indicator may include any of the short-term indicators as described above in reference to FIGS. 1-15. Long-term indicator may include any of the long-term indicators as described above in reference to FIGS. 1-15. For instance and without limitation, an ameliorative output such as a medication utilized for chest pains may include a short-term indicator that includes reversal of chest pains and a long-term indicator that includes relaxing blood vessel walls. In yet another non-limiting example, an ameliorative output such as a nutrition plan may include a short-term indicator that includes investment of resources in new ingredients and new cooking utensils and a long-term indicator that includes reduced risk of diabetes.

With continued reference to FIG. 15, at step 1515 at least a server receives at least a user life element datum 168 wherein the at least a user life element datum 168 further comprises at least a user life quality response 172. User life element datum 168 may include any of the user life element datums as described above in reference to FIGS. 1-15. User life element datum 168 may include data describing a user's life criterion including for example principles, standards, and/or goals that a user aspires to achieve. User life element datum 168 includes at least a user life quality response 172. User life quality response 172 includes any of the user life quality response 172 as described above in reference to FIGS. 1-15. User life quality response 172 may include a datum describing a user's preference to receive lifesaving medical treatment while unconscious or a user's preference to live out a terminal illness without medical treatment. User life element datum 168 may include a user ameliorative effort indicator datum. User ameliorative effort indicator datum may include any of the ameliorative effort indicator datums as described above in reference to FIGS. 1-15. For example, user ameliorative effort indicator datum may include a description of how much effort including resources, time, and energy that a user seeks to devote to a particular ameliorative output. For example, a user may seek to spend little time preparing fresh meals because user doesn't like to cook but user may seek to spend three hours each week practicing a meditation sequence. User life element datum 168 may include a user constitutional variance life datum. Constitutional variance life datum may include any of the constitutional variance life datums as described above in reference to FIGS. 1-15. For example, constitutional variance life datum may include a description of a user entered long term longevity goal such as to gain better control on migraine attacks or to feel less bloating in stomach after eating.

With continued reference to FIG. 15, at step 1520 at least a server generates a loss function of the plurality of short-term indicators and the plurality of long-term indicators using the at least a user life element datum. Loss function may include any of the loss functions as described above in reference to FIGS. 1-15. Generating a loss function may include generating a loss function utilizing any of the methodologies as described above in reference to FIGS. 1-15. Variables utilized to generate a loss function may include any of the variables as described above in reference to FIG. 12. For example, loss function module 180 may generate a loss function utilizing variables that include life element datum, life quality response 172, user ameliorative effort indicator datum, constitutional variance life datum, biological extractions, and miscellaneous variables. Generating loss function may include receiving at least a biological extraction from a user and generating the loss function as a function of the at least a biological extraction.

With continued reference to FIG. 15, at step 1525 at least a server 104 selects at least an ameliorative output from the plurality of ameliorative outputs to minimize the loss function. Minimizing a loss function may be done utilizing any of the methodologies as described above in reference to FIGS. 1-15. Loss function analysis algorithms may iterate to gradually converge towards a minimum where further tweaks to the parameters produce little or zero changes in the loss or convergence by optimizing weights utilized by machine learning algorithms. Loss function analysis may examine the cost of the difference between estimated values, to calculate the difference between hypothetical and real values. Loss function module 180 may utilize variables to model relationships between prognostic outputs, life element datums, life quality response 172, and ameliorative outputs and aid in selecting at least an ameliorative output.

With continued reference to FIG. 15, least a server may be configured to receive at least a first ameliorative output containing at least a short-term indicator and at least a long-term indicator, generate a plurality of ameliorative output neutralizers as a function of the at least an ameliorative output wherein the plurality of ameliorative output neutralizers include at least a short-term indicator and at least a long-term indicator, a generate a loss function as a function of the at least a first ameliorative output and the plurality of ameliorative output neutralizers, minimize the loss function, and select at least an ameliorative output neutralizer from the plurality of ameliorative output neutralizers as a function of minimizing the loss function. An ameliorative output neutralizer, includes any ameliorative output intended to minimize at least a long-term indicator containing a negative and/or unwanted consequence of at least a first ameliorative output. For instance and without limitation, a first ameliorative output such as a diabetes medication that includes a long-term indicator such as an increased risk of kidney failure may be selected to generate a plurality of ameliorative output neutralizers that may minimize the long-term indicator and reduce the risk of kidney failure. Plurality of ameliorative output neutralizers may be generated utilizing any of the machine-learning processes as described above in reference to FIGS. 1-15. In an embodiment, ameliorative process label learner may generate plurality of output neutralizers. At least a server 104 may generate a loss function as a function of at least a first ameliorative output and the plurality of ameliorative output neutralizers and minimize the loss function. Generating a loss function and minimizing the loss function may be done utilizing any of the methods as descried above in reference to FIGS. 1-15. At least an ameliorative output neutralizer may be selected as a function of minimizing the loss function.

With continued reference to FIG. 15, at least a server 104 selects at least an ameliorative output from a plurality of ameliorative outputs as a function of minimizing the loss function. In an embodiment, selecting at least an ameliorative output may performed by selector module 184 operating on at least a server 104. Selector module 184 may select at least an ameliorative output contained within loss function output by analyzing positives and negatives associated with ameliorative outputs as compared to prognostic outputs. For example, selector module 184 may balance prognostic output short-term output, prognostic output long-term output, ameliorative output short-term indicator, and/or ameliorative output long-term indicator to select an ameliorative output. Selector module 184 may at least an ameliorative output as a function of matching at least a prognostic output containing at least a long-term output to at least an ameliorative output containing at least a long-term indicator. For example, a prognostic output such as Celiac disease may contain at least a long-term output that includes reducing risk of fractures due to decreased calcium absorption caused by Celiac disease. In such an instance, reducing risk of fractures may be matched to at least an ameliorative output contained within loss function output that includes an ameliorative output containing at least a long-term indicator that doesn't include increased risk of fractures, or to at least a long-term indicator that includes increased calcium absorption. Selecting at least an ameliorative output from a plurality of ameliorative outputs may include receiving at least a datum of previous ameliorative history for a user and selecting at least an ameliorative output as a function of the at least a datum of previous ameliorative history. For example, at least a datum of previous ameliorative history such as a previous meditation sequence that a user performed to prophylactically ward off migraine headaches may be utilized to select at least an ameliorative output that includes a meditation sequence. In yet another non-limiting example, at least a datum of previous ameliorative history such as a previous meditation that a user consumed during pregnancy to reduce heart burn symptoms and that didn't cause any further pregnancy complications may be utilized by selector module 184 and/or at least a server 104 to select at least an ameliorative output containing previous medication when user experiences same symptoms with a subsequent pregnancy. In an embodiment, selector module 184 may select at least an ameliorative output from the plurality of ameliorative outputs as a function of ranking the plurality of ameliorative outputs as a function of at least a long-term indicator score. Long-term indicator may be matched and compared to a user constitutional variance life datum to evaluate if a user long-term goal matches up with a long-term indicator. For example, a user constitutional variance life datum that includes a user's desire to lose 10 pounds may not be matched to an ameliorative output containing a long-term indicator that includes weight gain. In yet another non-limiting example, a user constitutional variance life datum that includes a user's desire to exercise three days each week may be matched to an ameliorative output that includes a long-term indicator of increased muscle strength.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 16:
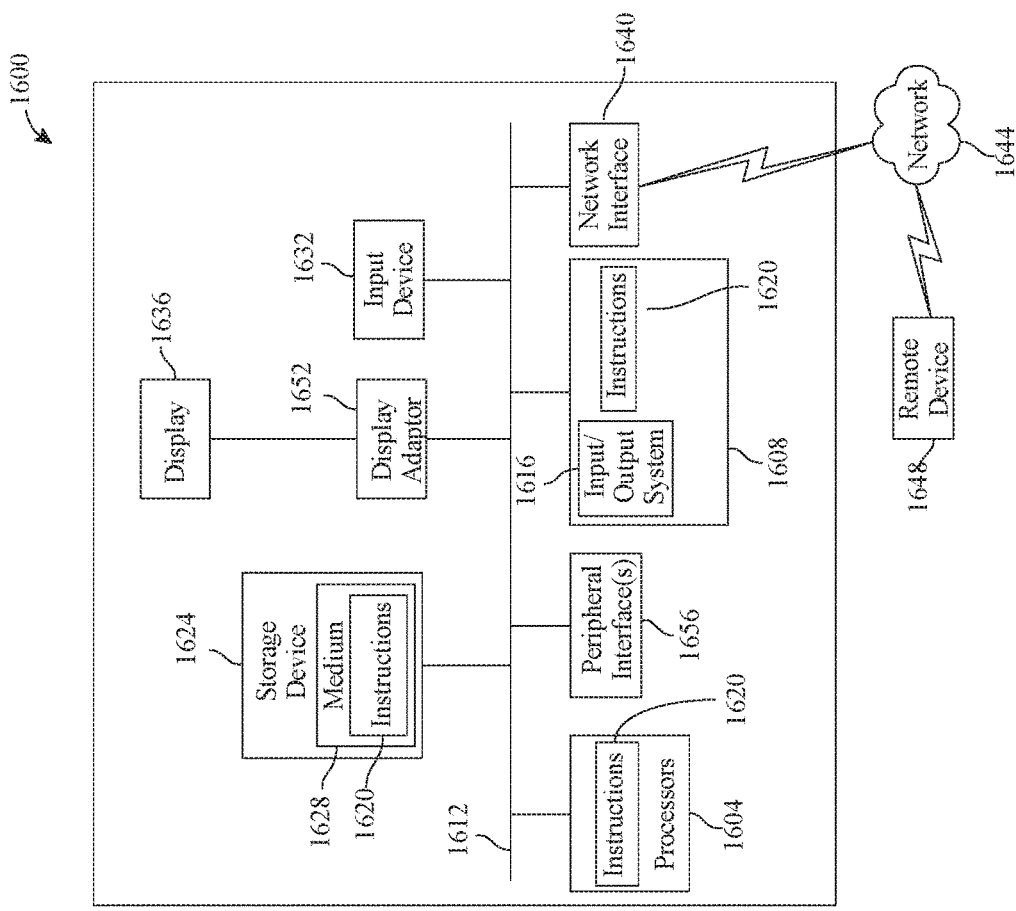
FIG. 16 is a block diagram of a computing system that can be used to implement any one or more of the methodologies disclosed herein and any one or more portions thereof.

FIG. 16 shows a diagrammatic representation of one embodiment of a computing device in the exemplary form of a computer system 1600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1600 includes a processor 1604 and a memory 1608 that communicate with each other, and with other components, via a bus 1612. Bus 1612 may include any of several types of bus structures including, but not limited to, a memory bus, a memory controller, a peripheral bus, a local bus, and any combinations thereof, using any of a variety of bus architectures.

Memory 1608 may include various components (e.g., machine-readable media) including, but not limited to, a random access memory component, a read only component, and any combinations thereof. In one example, a basic input/output system 1616 (BIOS), including basic routines that help to transfer information between elements within computer system 1600, such as during start-up, may be stored in memory 1608. Memory 1608 may also include (e.g., stored on one or more machine-readable media) instructions (e.g., software) 1620 embodying any one or more of the aspects and/or methodologies of the present disclosure. In another example, memory 1608 may further include any number of program modules including, but not limited to, an operating system, one or more application programs, other program modules, program data, and any combinations thereof.

Computer system 1600 may also include a storage device 1624. Examples of a storage device (e.g., storage device 1624) include, but are not limited to, a hard disk drive, a magnetic disk drive, an optical disc drive in combination with an optical medium, a solid-state memory device, and any combinations thereof. Storage device 1624 may be connected to bus 1612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1624 (or one or more components thereof) may be removably interfaced with computer system 1600 (e.g., via an external port connector (not shown)). Particularly, storage device 1624 and an associated machine-readable medium 1628 may provide nonvolatile and/or volatile storage of machine-readable instructions, data structures, program modules, and/or other data for computer system 1600. In one example, software 1620 may reside, completely or partially, within machine-readable medium 1628. In another example, software 1620 may reside, completely or partially, within processor 1604.

Computer system 1600 may also include an input device 1632. In one example, a user of computer system 1600 may enter commands and/or other information into computer system 1600 via input device 1632. Examples of an input device 1632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1632 may be interfaced to bus 1612 via any of a variety of interfaces (not shown) including, but not limited to, a serial interface, a parallel interface, a game port, a USB interface, a FIREWIRE interface, a direct interface to bus 1612, and any combinations thereof. Input device 1632 may include a touch screen interface that may be a part of or separate from display 1636, discussed further below. Input device 1632 may be utilized as a user selection device for selecting one or more graphical representations in a graphical interface as described above.

A user may also input commands and/or other information to computer system 1600 via storage device 1624 (e.g., a removable disk drive, a flash drive, etc.) and/or network interface device 1640. A network interface device, such as network interface device 1640, may be utilized for connecting computer system 1600 to one or more of a variety of networks, such as network 1644, and one or more remote devices 1648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1644, may employ a wired and/or a wireless mode of communication. In general, any network topology may be used. Information (e.g., data, software 1620, etc.) may be communicated to and/or from computer system 1600 via network interface device 1640.

Computer system 1600 may further include a video display adapter 1652 for communicating a displayable image to a display device, such as display device 1636. Examples of a display device include, but are not limited to, a liquid crystal display (LCD), a cathode ray tube (CRT), a plasma display, a light emitting diode (LED) display, and any combinations thereof. Display adapter 1652 and display device 1636 may be utilized in combination with processor 1604 to provide graphical representations of aspects of the present disclosure. In addition to a display device, computer system 1600 may include one or more other peripheral output devices including, but not limited to, an audio speaker, a printer, and any combinations thereof. Such peripheral output devices may be connected to bus 1612 via a peripheral interface 1656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for selecting an ameliorative output using artificial intelligence, the system comprising:
  at least a server housed with at least a sensor configured to detect physiological state data,
    the at least a server designed and configured to:

identify at least a prognostic output as a function of physiological state data,
  wherein identifying the at least a prognostic output further comprises:
    creating at least a prognostic machine learning model correlating a plurality of physiological state data to prognostic labels by:
      generating a first training data set, wherein the first training data set correlates historical physiological state data to historical prognostic labels based on a distance between the historical physiological state data and the historical prognostic labels within an ordered collection of data, and wherein generating the first training data set further comprises removing an entry of the first training data set in response to detecting the physiological state data; and
      training the prognostic machine learning model utilizing the first training data set; and
    generating the at least a prognostic output utilizing the trained prognostic machine learning model;
  generate a plurality of ameliorative outputs, the plurality of ameliorative outputs associated with a plurality of short-term indicators and a plurality of long-term indicators, as a function of the at least a prognostic output wherein each ameliorative output of the plurality of ameliorative outputs includes at least a short-term indicator of the plurality of short-term indicators and at least a long-term indicator of the plurality of long-term indicators;
  receive at least a user life element datum wherein the at least a user life element datum further comprises at least a user life quality response;
  generate a loss function of the plurality of short-term indicators and the plurality of long-term indicators using the at least a user life element datum; and
  select at least an ameliorative output from the plurality of ameliorative outputs to minimize the loss function.

2. The system of claim 1, wherein generating a plurality of ameliorative outputs further comprises:
  selecting at least a training set as a function of the at least a prognostic output; and
  generating a machine-learning process as a function of the at least a prognostic output and the at least a training set.

3. The system of claim 1, wherein the at least a user life element datum further comprises at least a user ameliorative effort indicator datum.

4. The system of claim 1, wherein the at least a user life element further comprises at least a user constitutional variance life datum.

5. The system of claim 1, wherein the at least a server is further configured to:
  receive at least a biological extraction from a user; and
  generate the loss function using the at least a biological extraction.

6. The system of claim 1, wherein the at least a server is further configured to:
  receive at least a datum of previous ameliorative history for a user; and
  select at least an ameliorative output as a function of the at least a datum of previous ameliorative history.

7. The system of claim 1, wherein the at least a server is further configured to select at least an ameliorative output as a function of matching the at least a prognostic output containing at least a long-term output to at least an ameliorative output containing the at least a long-term indicator.

8. The system of claim 1, wherein the at least a server is further configured to select at least an ameliorative output as a function of ranking the plurality of ameliorative outputs as a function of the at least a long-term indicator and selecting at least an ameliorative output as a function of ranking.

9. The system of claim 1, wherein the at least a server is further configured to select at least an ameliorative output as a function of matching at least a user constitutional variance life datum to at least an ameliorative output containing at least a long-term indicator.

10. The system of claim 1, wherein the at least a server is further configured to:
  receive at least a first ameliorative output containing the at least a short-term indicator and the at least a long-term indicator;
  generate a plurality of ameliorative output neutralizers the plurality of ameliorative output neutralizers associated with the plurality of short-term indicators and the plurality of long-term indicators, as a function of the at least a first ameliorative output wherein each ameliorative output neutralizer of the plurality of ameliorative output neutralizers includes the at least a short-term indicator of the plurality of short-term indicators and the at least a long-term indicator of the plurality of long-term indicators;
  generate a loss function of the plurality of short-term indicators and the plurality of long-term indicators using the at least a first ameliorative output; and
  select at least an ameliorative output neutralizer from the plurality of ameliorative output neutralizers to minimize the loss function.

11. A method of selecting an ameliorative output using artificial intelligence the method comprising:
  identifying by at least a server housed with at least a sensor configured to detect physiological state data, at least a prognostic output as a function of physiological state data, wherein identifying the at least a prognostic output further comprises:
    creating at least a prognostic machine learning model correlating a plurality of physiological state data to prognostic labels by:
      generating a first training data set, wherein the first training data set correlates historical physiological state data to historical prognostic labels based on a distance between the historical physiological state data and the historical prognostic labels within an ordered collection of data, and wherein generating the first training data set further comprises removing an entry of the first training data set in response to detecting the physiological state data; and
      training the prognostic machine learning model utilizing the first training data set; and
    generating the at least a prognostic output utilizing the trained prognostic machine learning model;
  generating by the at least a server a plurality of ameliorative outputs, the plurality of ameliorative outputs associated with a plurality of short-term indicators and a plurality of long-term indicators, as a function of the at least a prognostic output wherein each ameliorative output of the plurality of ameliorative outputs includes at least a short-term indicator of the plurality of short-term indicators and at least a long-term indicator of the plurality of long-term indicators;

receiving by the at least a server at least a user life element datum wherein the at least a user life element datum further comprises at least a user life quality response;

generating by the at least a server a loss function of the plurality of short-term indicators and the plurality of long-term indicators using the at least a user life element datum; and selecting by the at least a server at least an ameliorative output from the plurality of ameliorative outputs to minimize the loss function.

12. The method of claim 11, wherein generating a plurality of ameliorative outputs further comprises:
selecting at least a training set as a function of the at least a prognostic output; and
generating a machine-learning process as a function of the at least a prognostic output and the at least a training set.

13. The method of claim 11, wherein receiving at least a user life element datum further comprises receiving at least a user ameliorative effort indicator datum.

14. The method of claim 11, wherein receiving at least a user life element datum further comprises receiving at least a user constitutional variance life datum.

15. The method of claim 11, wherein receiving at least a user life element datum further comprises:
receiving at least a biological extraction from a user; and
generating the loss function using the at least a biological extraction.

16. The method of claim 11, wherein selecting at least an ameliorative output further comprises:
receiving at least a datum of previous ameliorative history for a user; and
selecting at least an ameliorative output as a function of the at least a datum of previous ameliorative history.

17. The method of claim 11, wherein selecting at least an ameliorative output further comprises matching the at least a prognostic output containing at least a long-term output to at least an ameliorative output containing the at least a long-term indicator.

18. The method of claim 11, wherein selecting at least an ameliorative output further comprises ranking the plurality of ameliorative outputs as a function of the at least a long-term indicator and selecting at least an ameliorative output as a function of ranking.

19. The method of claim 11, wherein selecting at least an ameliorative output further comprises matching at least a user constitutional variance life datum to at least an ameliorative output containing at least a long-term indicator.

20. The method of claim 11 further comprising:
receiving at least a first ameliorative output containing the at least a short-term indicator and the at least a long-term indicator;
generating a plurality of ameliorative output neutralizers the plurality of ameliorative output neutralizers associated with the plurality of short-term indicators and the plurality of long-term indicators, as a function of the at least a first ameliorative output wherein each ameliorative output neutralizer of the plurality of ameliorative output neutralizers includes the at least a short-term indicator of the plurality of short-term indicators and the at least a long-term indicator of the plurality of long-term indicators;
generating a loss function of the plurality of short-term indicators and the plurality of long-term indicators using the at least a first ameliorative output; and
selecting at least an ameliorative output neutralizer from the plurality of ameliorative output neutralizers to minimize the loss function.

* * * * *